United States Patent [19]
Creighton et al.

[11] Patent Number: 5,969,174
[45] Date of Patent: Oct. 19, 1999

[54] COMPETITIVE INHIBITORS OF GLYOXALASE I AND METHOD OF GENERATING SUCH COMPETITIVE INHIBITORS INSIDE TUMOR CELLS

[75] Inventors: Donald Creighton, Baltimore; Malcolm J. Kavarana, Ellicott City; Diana S. Hamilton, Catonsville, all of Md.

[73] Assignee: University of Maryland at Baltimore County, Baltimore, Md.

[21] Appl. No.: 09/003,835

[22] Filed: Jan. 7, 1998

[51] Int. Cl.⁶ .................................................. C07C 333/00
[52] U.S. Cl. .......................... 558/232; 514/365; 514/415; 548/146; 546/201; 549/29; 549/200; 560/312
[58] Field of Search ...................... 558/230, 232, 558/241, 243, 250, 252; 514/365, 415; 548/146; 546/201; 549/29, 200; 560/312

[56] References Cited

U.S. PATENT DOCUMENTS 5,616,563 4/1997 Creighton .................................. 514/18

Primary Examiner—Cecilia J. Tsang
Assistant Examiner—David Lukton
Attorney, Agent, or Firm—Benjamin Aaron Adler

[57] ABSTRACT

The present invention provides a compound having the structure

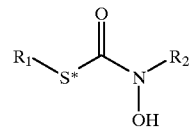

wherein $S^*$ is $S=O$ or $O=S=O$; and wherein $R_1$ is selected from the group consisting of $(C_1-C_9)$ alkyl, $(C_3-C_8)$ cycloalkyl, $(C_5-C_7)$ cycloalkenyl, and $(C_6-C_{20})$ aryl substituted with halogen or $(C_1-C_{18})$ alkyl; and wherein $R_2$ is selected from the group consisting of alkyl, $(C_1-C_9)$ alkyl, $(C_3-C_8)$ cycloalkyl, $(C_5-C_7)$ cycloalkenyl, and $(C_6-C_{20})$ aryl substituted with halogen or $(C_1-C_{18})$ alkyl. Also provided are various methods of using the compositions of the present invention.

20 Claims, 16 Drawing Sheets

1: X=H, R=H         1(Et)₂:  X=H, R=C₂H₅

2: X=Cl, R=H        2(Et)₂:  X=H, R=C₂H₅

3: X=Br, R=H        3(Et)₂:  X=H, R=C₂H₅

COMPETITIVE INHIBITORS OF GLYOXALASE I AND METHOD OF GENERATING SUCH COMPETITIVE INHIBITORS INSIDE TUMOR CELLS

FEDERAL FUNDING LEGEND

This invention was created in part using funds from the federal government under a grant from the National Institutes of Health (CA 59612). The U.S. government, therefore, has certain rights in this invention.

BACKGROUND OF THE INVENTION

1. Field of the Invention

The present invention relates generally to the fields of chemistry and antineoplastic pharmacology. More specifically, the present invention relates to competitive inhibitors of glyoxalase I and methods of generating such competitive inhibitors inside tumor cells.

2. Description of the Related Art

Recent advances in understanding methylglyoxal metabolism suggest that the glyoxalase pathway might be a reasonable target for antitumor drug development (1). The apparent physiological function of this pathway is to remove cytotoxic methylglyoxal from cells as D-lactate via the sequential action of the isomerase glyoxalase I (GlxI) and the thioester hydrolase glyoxalase II (GlxII), FIG. 1. Methylglyoxal appears to arise primarily as a by-product of the interconversion of intracellular triosephosphates, as well as from other sources (3,4). High concentrations of exogenous methylglyoxal exhibit selective inhibitory activity toward rapidly proliferating tumor cells versus nonproliferating normal cells in vitro (5–8). The molecular basis of methylglyoxal toxicity is not clearly understood, but may involve inhibition of DNA and protein synthesis (5,9). Indeed, methylglyoxal is known to form adducts with nucleic acids (10). Supporting a detoxification role for the glyoxalase pathway is the demonstration that transfected murine NIH3T3 cells that overexpress the gene for GlxI are exceptionally resistant to the cytotoxic effects of exogenous methylglyoxal (11).

Vince and Daluge suggested that inhibitors of GlxI might function as antitumor agents by inducing elevated levels of methylglyoxal in cells (12). Although numerous GSH-based competitive inhibitors have been described, a method for efficiently delivering these compounds into cells has not been available (2). Importantly, Lo and Thornalley reported that the competitive inhibitor S-p-bromobenzylglutathione can be indirectly delivered into human leukemia (HL60) cells as the [glycyl, glutamyl] diethyl ester prodrug, and that this compound is both cytostatic and cytotoxic to these cells (13). This prodrug strategy functions on the basis that after the diethyl ester diffuses into the cells, nonspecific esterases catalyze the deethylation of the diethyl ester to give the inhibitory diacid. The same laboratory reported that S-p-bromobenzylglutathione diethyl ester is toxic to a range of different human tumor cell lines in culture.

In any event, this prior art prodrug strategy is limited in at least two respects. First, the diffusion of the diethyl esters into cells is a relatively slow process. For example, the apparent first order rate constant for diffusion of 2Et)$_2$ into L1210 cells in vitro is only 0.04 min$^{-1}$ at 37° C. This probably reflects the fact that 2Et)$_2$ is a cationic species under physiological conditions, with limited solubility in the lipid bilayer of the cell membrane. Second, in contrast to human plasma, the plasma of most common strains of tumor-bearing laboratory mice contain high levels of plasma esterases which catalyze rapid deethylation of the diethyl ester prodrugs, T$_{1/2}$<30 sec. Therefore, costly esterase-deficient tumor-bearing mice are required in order to evaluate the in vivo antitumor activities of the diethyl ester prodrugs.

The prior art is deficient in the lack of effective means of delivering competitive inhibitors of the methylglyoxal-detoxifying enzyme glyoxalase I into cells. The present invention fulfills this longstanding need and desire in the art.

SUMMARY OF THE INVENTION

An efficient method has been discovered for indirectly delivering an inhibitor of the methylglyoxal-detoxifying enzyme glyoxalase I into cells via an acyl-interchange reaction between the prodrug S-(N-p-chlorophenyl-N-hydroxycarbamoyl)ethylsulfoxide and intracellular glutathione. The second order rate constant for the acyl-interchange reaction in a cell-free system is 1.84 mM$^{-1}$ min.$^{-1}$ (100 mM potassium phosphate buffer, 5% ethanol, pH 7.5, 25° C.). Incubation of L1210 cells with the sulfoxide results in a rapid increase in the intracellular concentration of the glyoxalase I inhibitor, with an apparent first order rate constant of 1.41±0.03 min$^{-1}$. This reflects rapid diffusion of the sulfoxide across the cell membrane followed by acyl-interchange with intracellular glutathione. The maximum achievable concentration of inhibitor inside the cells is about 10-fold larger than the extracellular concentration of sulfoxide. In addition, the sulfoxide is approximately 10-fold more potent (IC$_{50}$=0.8±0.5 µM) toward L1210 cells in vitro than a previously described prodrug S-(N-p-chlorophenyl-N-hydroxycarbamoyl)glutathione diethyl ester. The sulfoxide is reasonably stable in serum from DBA/2 mice, T$_{1/2}$=13±2 minutes (n=3).

The present invention discloses a more efficient method for generating enediol analog I inside cells via an acyl-interchange reaction between intracellular glutathione and the membrane-permeable prodrug S-(N-p-chlorophenyl-N-hydroxycarbamoyl)ethyl sulfoxide. The increased efficiency of delivery is associated with a corresponding increase in potency. Moreover, this prodrug strategy avoids some of the bioavailability problems associated with evaluating antitumor activities in tumor-bearing mice containing high plasma esterase activities.

In one embodiment of the present invention, there is provided a compound having the structure

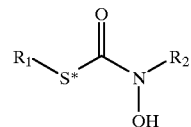

wherein S* is S=O or O=S=O; R$_1$ is Z$_1$ or Ar$_1$; R$_2$ is independently Z$_1$ or Ar$_1$; wherein Z$_1$ is optionally substituted with Z$_2$ or Z$_3$, Z$_2$ is optionally substituted with Z$_3$, Ar$_1$ is optionally substituted with Z$_4$; and wherein Z$_1$ is a C$_1$–C$_9$ straight or branched chain alkyl or alkenyl group; Z$_2$ is C$_3$–C$_8$ cycloalkyl or C$_5$–C$_7$ cycloalkenyl; Z$_3$ is C$_1$–C$_4$ alkyl, C$_1$–C$_4$ alkenyl, or hydroxyl; Z$_4$ is halo, hydroxyl, nitro, trifluoromethyl, optionally branched C$_1$–C$_6$ alkyl, optionally branched C$_1$–C$_6$ alkenyl, C$_1$–C$_4$ alkoxy, C$_1$–C$_4$ alkenyloxy, phenoxy, benzyloxy or amino; Ar$_1$ is selected from the group consisting of 1- or 2-naphthyl, 2- or 3-indolyl, 2- or 3-furyl, 2-thiazolyl, 2- or 3-thienyl, 2-, 3-, or 4-pyridyl, and phenyl; or pharmaceutically acceptable salts or hydrates thereof.

In another embodiment of the present invention, there is provided a pharmaceutical composition, comprising a compound disclosed herein and a pharmaceutically acceptable carrier.

In yet another embodiment of the present invention, there is provided a method of treating an individual having a neoplastic condition comprising the step of administering to said individual a pharmacologically effective dose of the composition disclosed herein.

In still yet another embodiment of the present invention, there is provided a method of inhibiting the growth of a tumor cell comprising the step of contacting said cell with a pharmacologically effective dose of the composition disclosed herein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

Conditions: RPMI 1640 medium containing 10% heat-inactivated fetal calf serum, 37° C.

Figure 10:
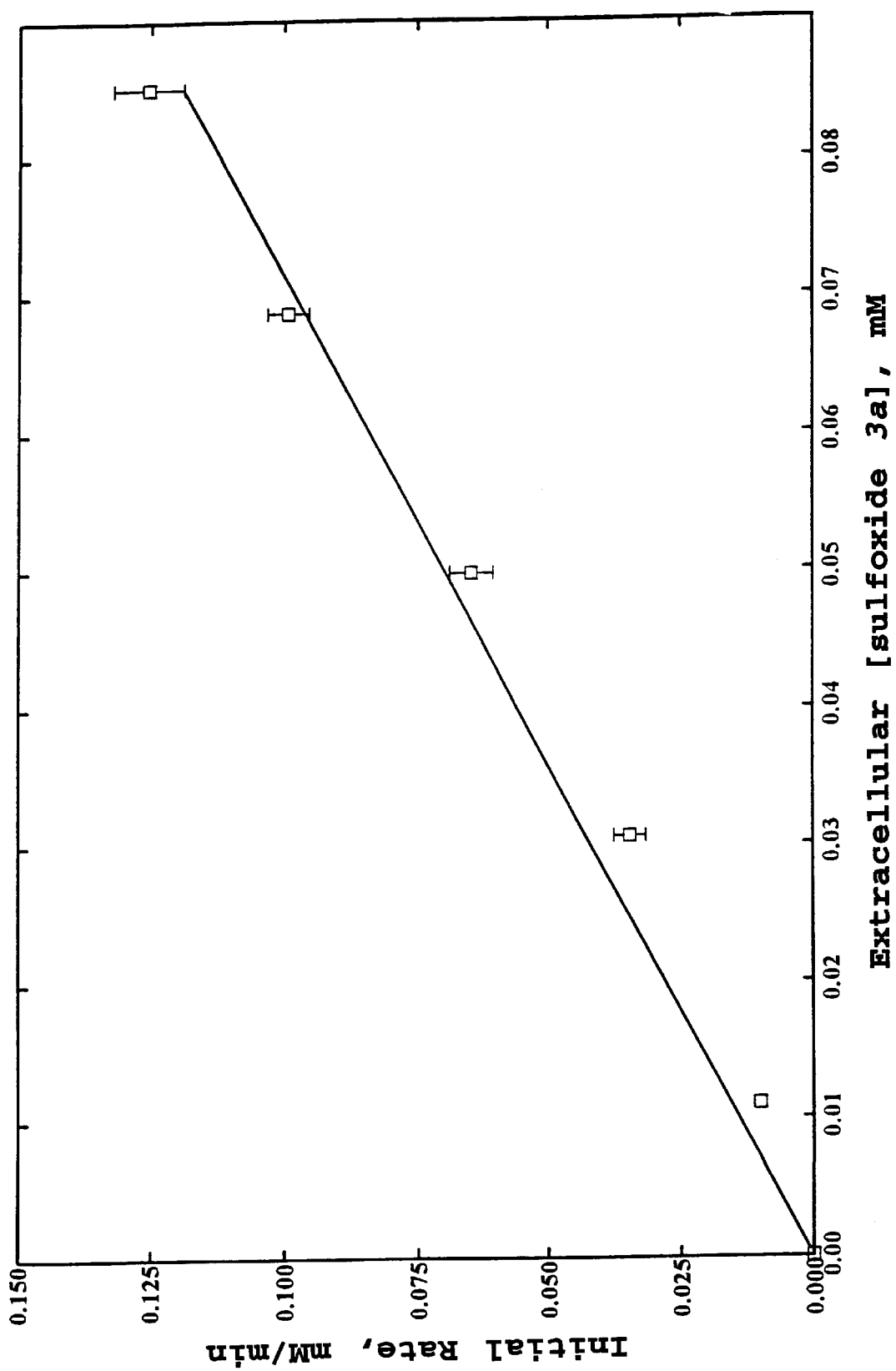

FIG. 10 shows the initial rates of appearance of intracellular of S-(N-p-chlorophenyl N-hydroxycarbamoyl) glutathione (1) in L1210 cells as a function of the extracellular concentration of sulfoxide 3a. Error bars represent standard deviations for triplicate determinations. Conditions: RPMI 1640 medium containing 10% heat-inactivated fetal calf serum, 37° C.

Figure 11:
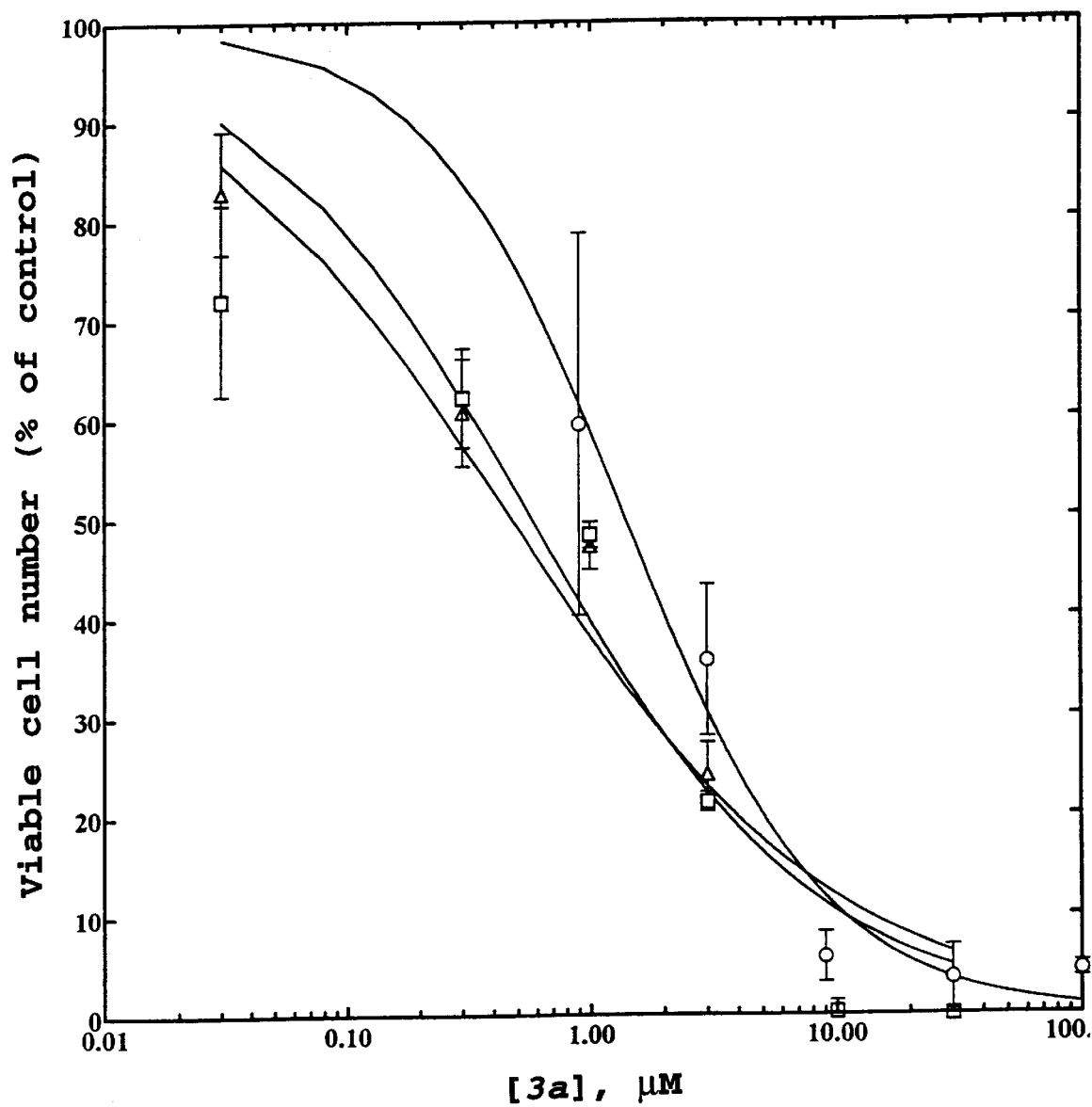

FIG. 11 shows the dose-response curve for L1210 cells with S-(N-p-chlorophenyl N-hydroxycarbamoyl) ethysulfoxide (3a). Error bars represent standard deviations for triplicate determinations. Different symbols correspond to experiments carried out on different days.

Figure 12:
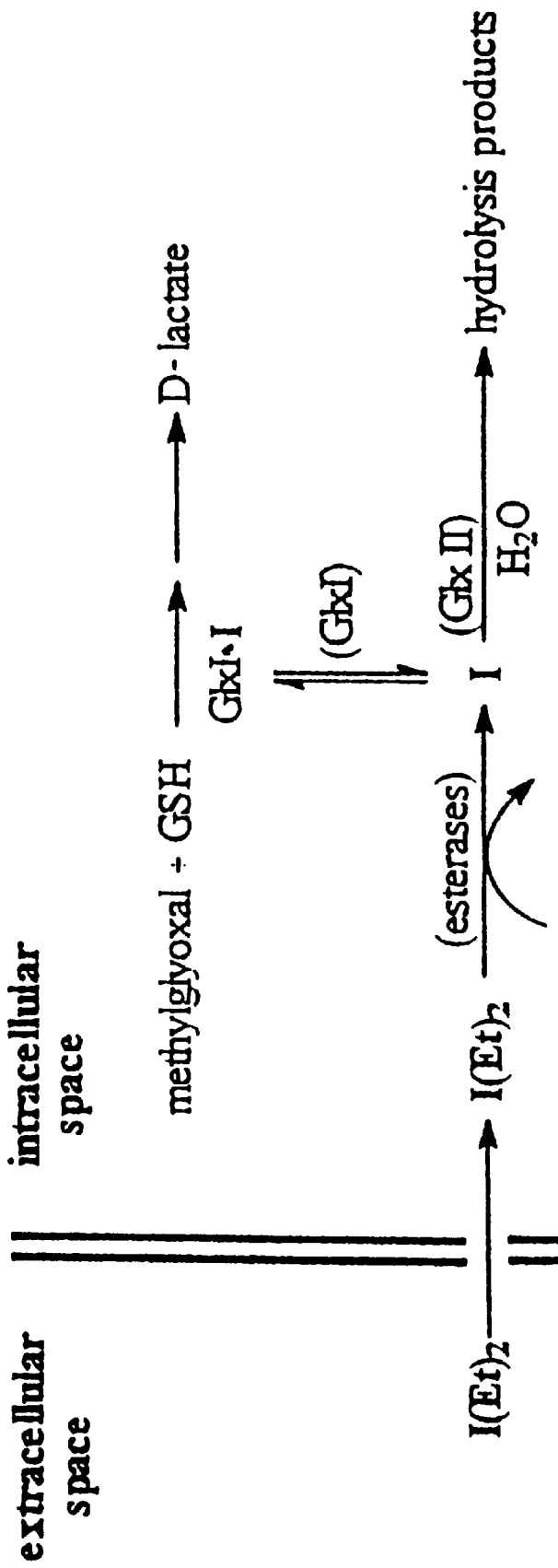

FIG. 12 shows the prodrug strategy for delivering the competitive inhibitors (I) of glyoxalase I (GlxI) into cells as the diethyl esters (I(Et)$_2$). Once inside the cell, the inhibitor can either bind to intracellular GlxI, causing the build-up of cytotoxic methylglyoxal, or be hydrolyzed by GlxII.

Figure 13:
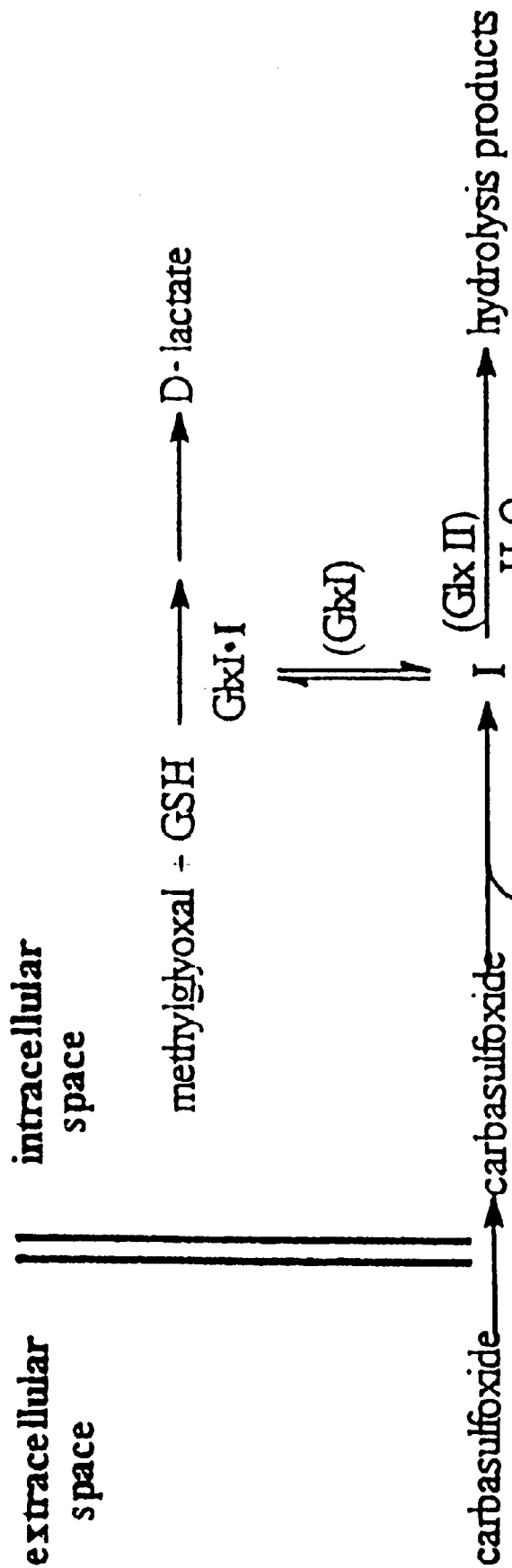

FIG. 13 shows the prodrug strategy for delivering the competitive inhibitors (I) of glyoxalase I (GlxI) into tumor cells via acyl-interchange between the membrane permeable carbasulfoxide and intracellular glutathione (GSH).

DETAILED DESCRIPTION OF THE INVENTION

In the present invention, the following abbreviations may be used: GlxI, glyoxalase I; GlxII, glyoxalase II; IC$_{50}$, concentration required to inhibit cell growth by 50% relative to no-drug controls; HPLC, high-performance liquid chromatography.

The present invention is directed to a compound having the structure

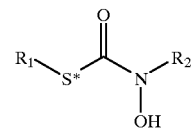

wherein S* is S=O or O=S=O; R$_1$ is Z$_1$ or Ar$_1$; R$_2$ is independently Z$_1$ or Ar$_1$; wherein Z$_1$ is optionally substituted with Z$_2$ or Z$_3$, Z$_2$ is optionally substituted with Z$_3$, Ar$_1$ is optionally substituted with Z$_4$, and wherein Z$_1$ is a C$_1$–C$_9$ straight or branched chain alkyl or alkenyl group; Z$_2$ is C$_3$–C$_8$ cycloalkyl or C$_5$–C$_7$ cycloalkenyl; Z$_3$ is C$_1$–C$_4$ alkyl, C$_1$–C$_4$ alkenyl, or hydroxyl; Z$_4$ is halo, bydroxyl, nitro, trifluoromethyl, optionally branched C$_1$–C$_6$ alkyl, optionally branched C$_1$–C$_6$ alkenyl, C$_1$–C$_4$ alkoxy, C$_1$–C$_4$ alkenyloxy, phenoxy, benzyloxy or amino; Ar$_1$ is selected from the group consisting of 1- or 2-naphthyl, 2- or 3-indolyl, 2- or 3-furyl, 2-thiazolyl, 2- or 3-thienyl, 2-, 3-, or 4-pyridyl, and phenyl; or pharmaceutically acceptable salts or hydrates thereof.

A person having ordinary skill in this art would readily recognize that the compounds of the present invention can be used as pharmaceutical compositions as using the prodrug strategy described in detail herein. Such pharmaceutical compositions would include the compounds of the present invention and a pharmaceutically acceptable carrier. Preferably, the pharmaceutical composition is administered in a dose of from about 0.1 mg/kg to about 25 mg/kg.

The present invention is also directed to methods of treating an individual having a neoplastic condition comprising the step of administering to said individual a pharmacologically effective dose of a composition described herein. Preferably, the composition is administered in a dose of from about 0.1 mg/kg to about 25 mg/kg. Although the compositions of the present invention may certainly be administered in any favorable fashion, common routes include that the composition is administered orally, intravenously, subcutaneously, transdermally, intramuscularly or intraperitoneally. Generally, the compositions of the present invention may be useful in treating any cancerous conditions. Representative examples of such cancers include renal cancer, ovarian cancer, lung cancer, glioma and leukemia.

The present invention is also directed to a method of inhibiting the growth of a tumor cell comprising the step of contacting said cell with a pharmacologically effective dose of the composition of described herein. Representative examples of tumor cells which can be treated include, but are not limited to, renal cancer cells, ovarian cancer cells, lung cancer cells, glioma cells and leukemia cells. Preferably, the composition is administered in a dose of from about 0.1 mg/kg to about 25 mg/kg.

The following examples are given for the purpose of illustrating various embodiments of the invention and are not meant to limit the present invention in any fashion.

EXAMPLE 1
Glyoxalase Activities in L1210 Cells and Splenic Lymphocytes

Cell pellets, containing approximately $2 \times 10^7$ L1210 cells or approximately $7 \times 10^7$ splenic lymphocytes, were lysed in 0.5 ml ice-cold sodium phosphate buffer (50 mM, pH 7.0) using a Potter-Elvehjem tissue grinder. Cell debris was removed by centrifugation at 13,000×g (20 min) at 4° C. The $V_{max}$ units of GlxI and GlxII in the supernatant fractions were obtained on the basis of hyperbolic fits of the initial rate data to the Michaelis-Menten expression. For GlxI, the initial rates of formation of S-D-lactoylglutathione versus [GSH-methylglyoxal thiohemiacetal] were followed at 240 nm ($\Delta\epsilon_{240}$ =2860 $M^{-1}$ $cm^{-1}$) in sodium phosphate buffer (50 mM, pH 7.0, 25° C.), maintaining free GSH at 0.1 mM (16). For GlxII, the initial rates of loss of S-D-lactoylglutathione versus [S-D-lactoylglutathione] were followed at 240 nm ($\epsilon_{240}$=3300 $M^{-1}$ $cm^{-1}$) in phosphate buffer (50 mM, pH 7.0, 25° C.). The concentrations of protein in the supernatant fractions were determined by the Bradford method, using bovine serum albumin as the reference standard (19).

EXAMPLE 2
Stability of 2(Et)$_2$ in Human Serum and Mouse Serum

To 0.5 ml portions of either human serum or mouse serum, at 37° C., was added compound 2(Et)$_2$ to an initial concentration of approximately 0.15 mM. As a function of time, 0.1 ml aliquots of the incubation mixture were transferred to separate microfuge tubes. The samples were immediately deproteinized by the addition of 70% ethanol (0.9 ml). After incubation for 30 minutes at 37° C., the protein precipitate was sedimented by centrifugation at 13,000 $\mu$g. The supernatants were then fractionated by reverse-phase HPLC, as described above, and the integrated intensities of the peaks corresponding to 2(Et)$_2$ determined. The rate constants for deethylation were calculated from the first-order rate of loss of 2(Et)$_2$ as a function of time.

EXAMPLE 3
Cytotoxicity Studies

Figure 1:
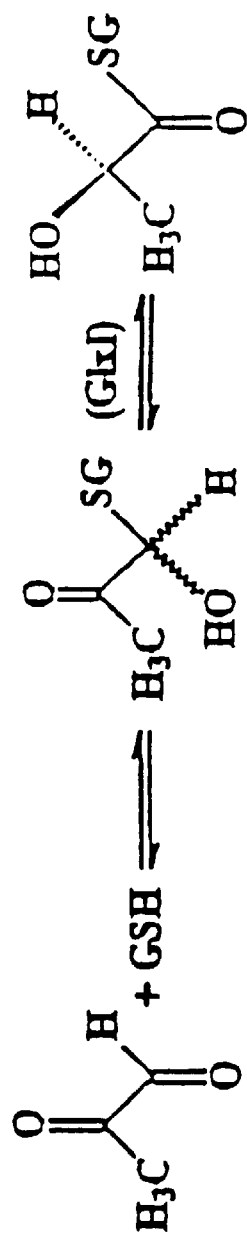
FIG. 1 shows the glyoxalase enzyme system. Symbols:GSH, glutathione (γ-L-Glu-L-CysGly); GlxI, glyoxalase I(EC 4.4.1.5); GlxII, glyoxalase II(EC 3.1.2.6).
Figure 1:
Figure 1:
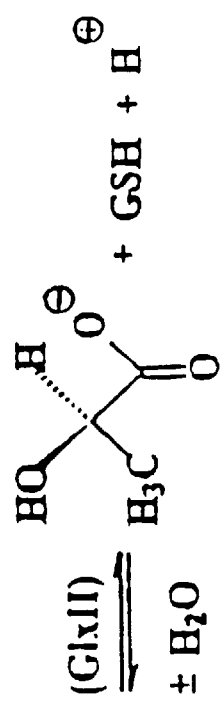
Figure 2:
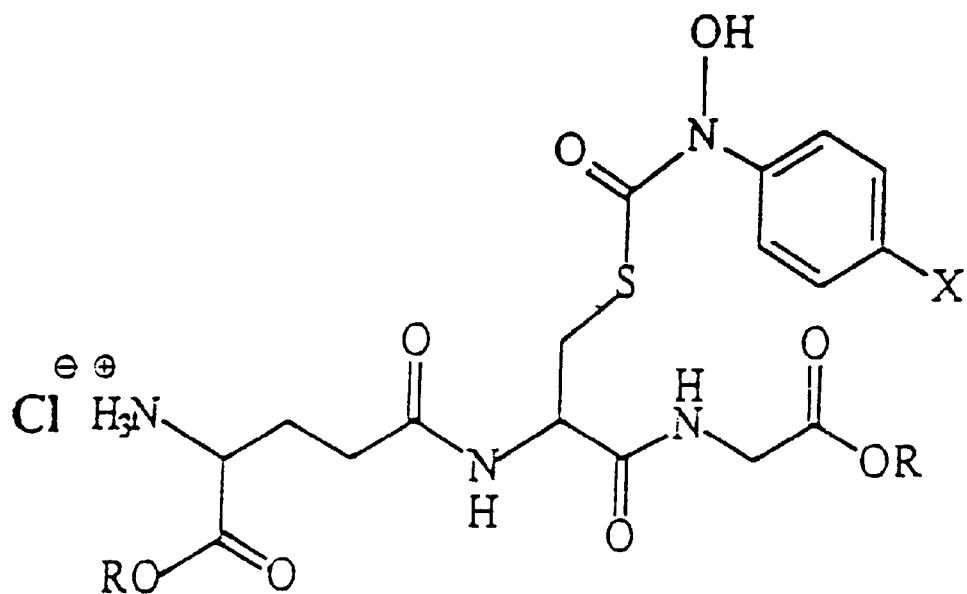
FIG. 2 shows the S-(N-aryl-N-hydroxycarbamoyl) glutathione derivatives (R=H) and their [glycyl, glutamyl] diethyl esters (R=$C_2H_5$).
Figure 3A:
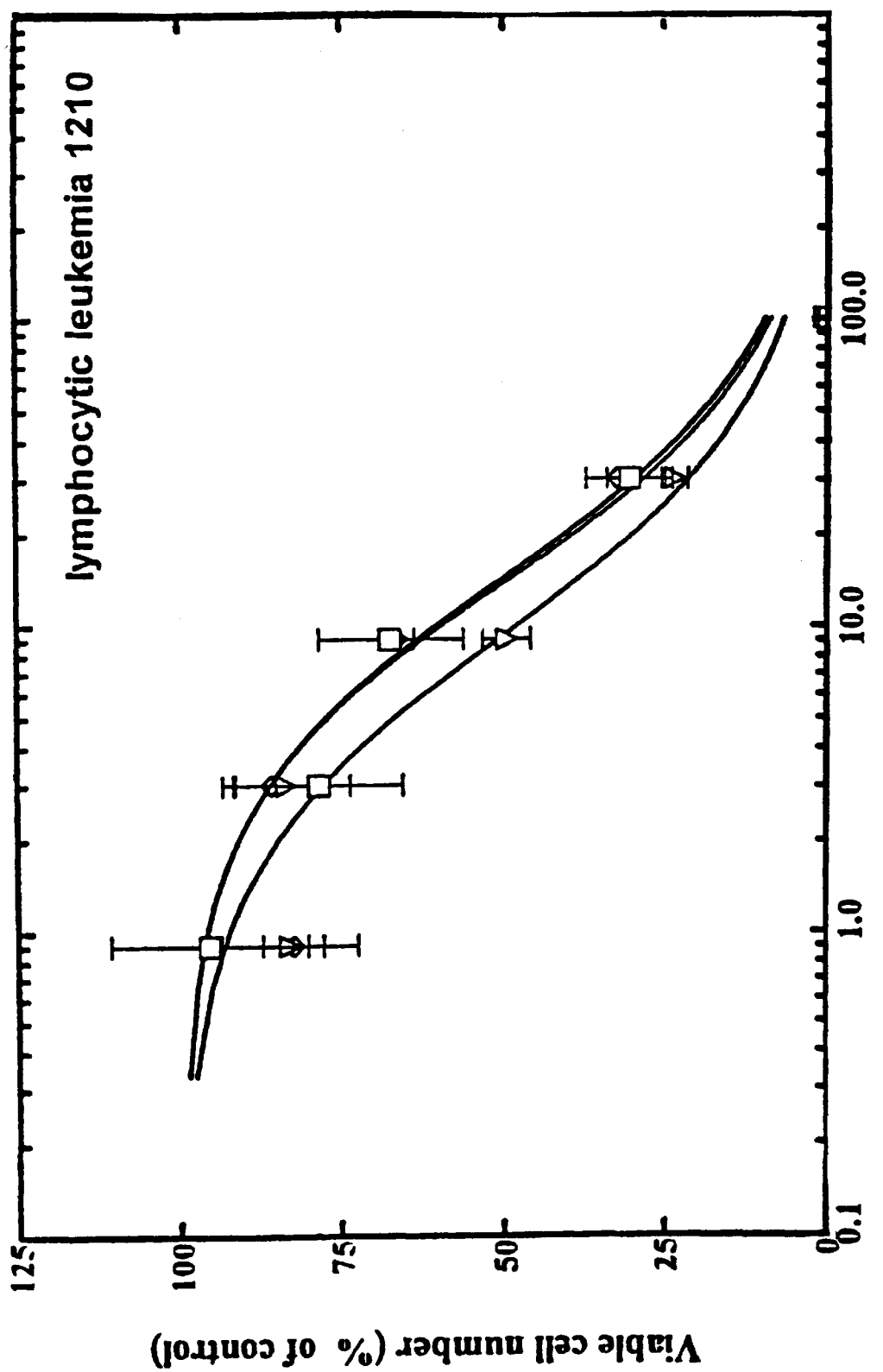
FIGS. 3A–3D shows the dose-response curves for L1210 cells and for splenic lymphocytes with S-(N-p-chlorophenyl N-hydroxycarbamoyl)glutathione (2(Et)$_2$) (panels A and B) and with S-p-bromobenzylglutathione diethyl ester (panels C and D) (48 h incubation period). Conditions: See Table 1. Error bars represent standard deviations for triplicate determinations. Different symbols correspond to experiments carried out on different days.
Figure 3B:
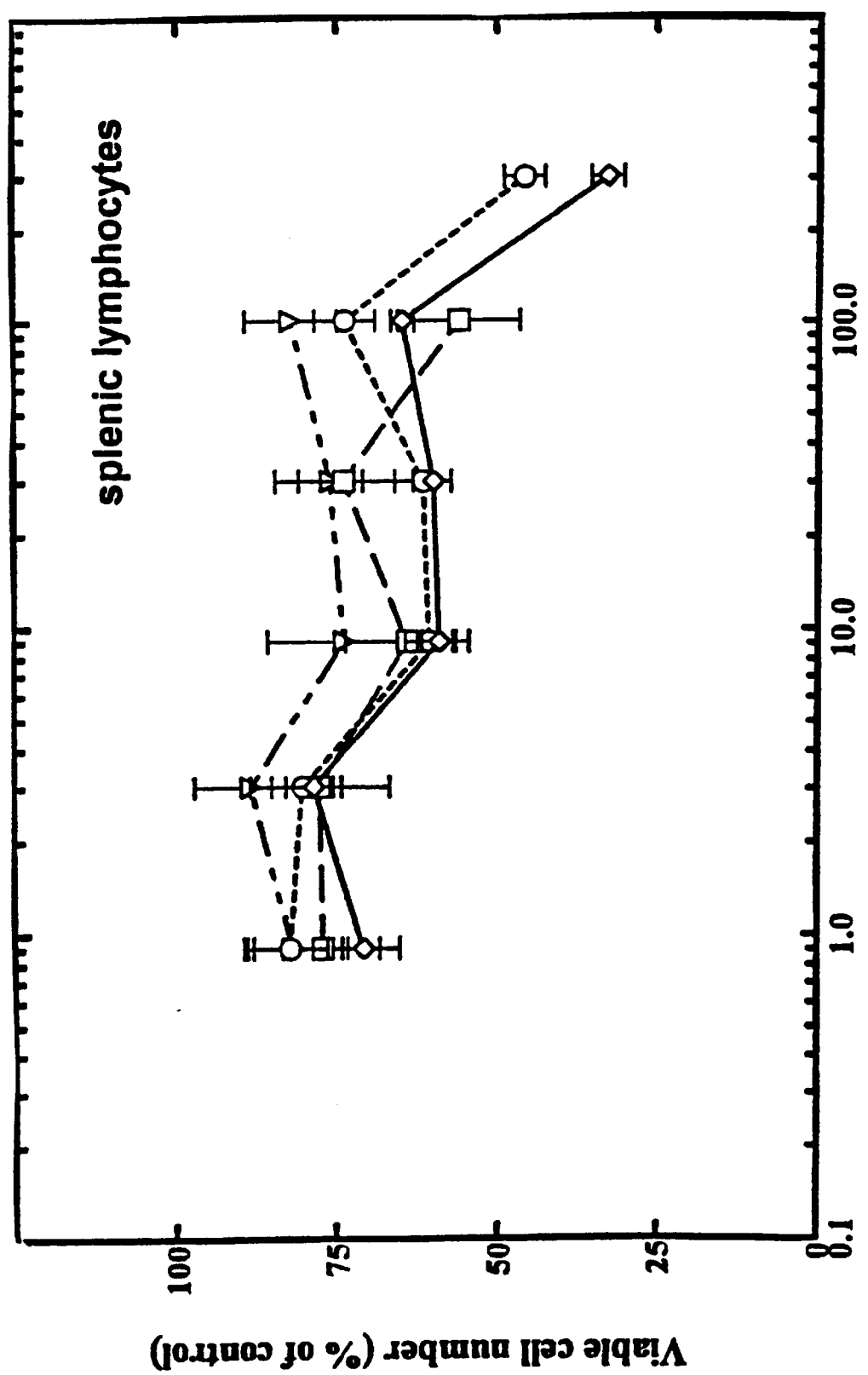
Figure 3C:
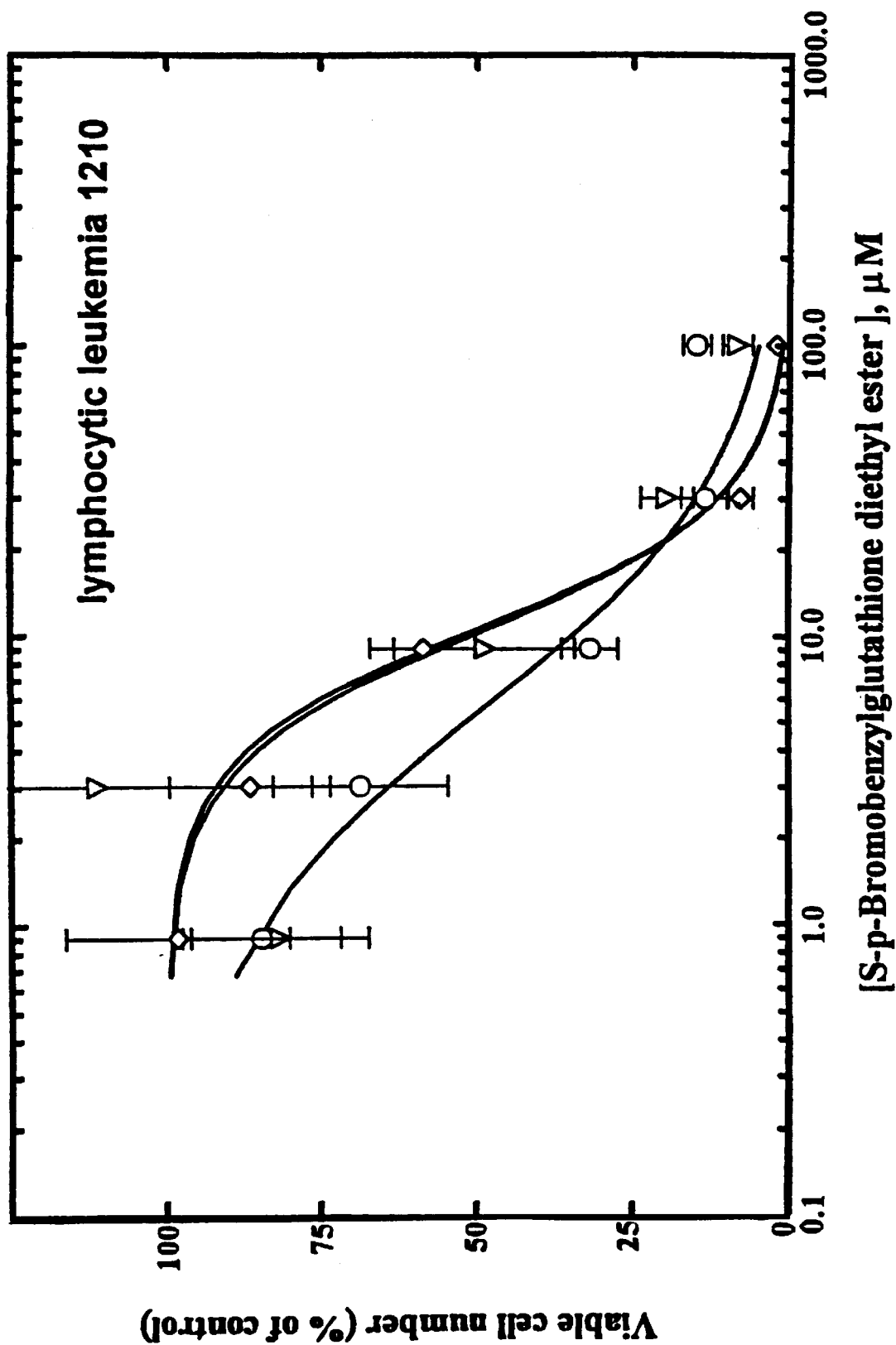
Figure 3D:
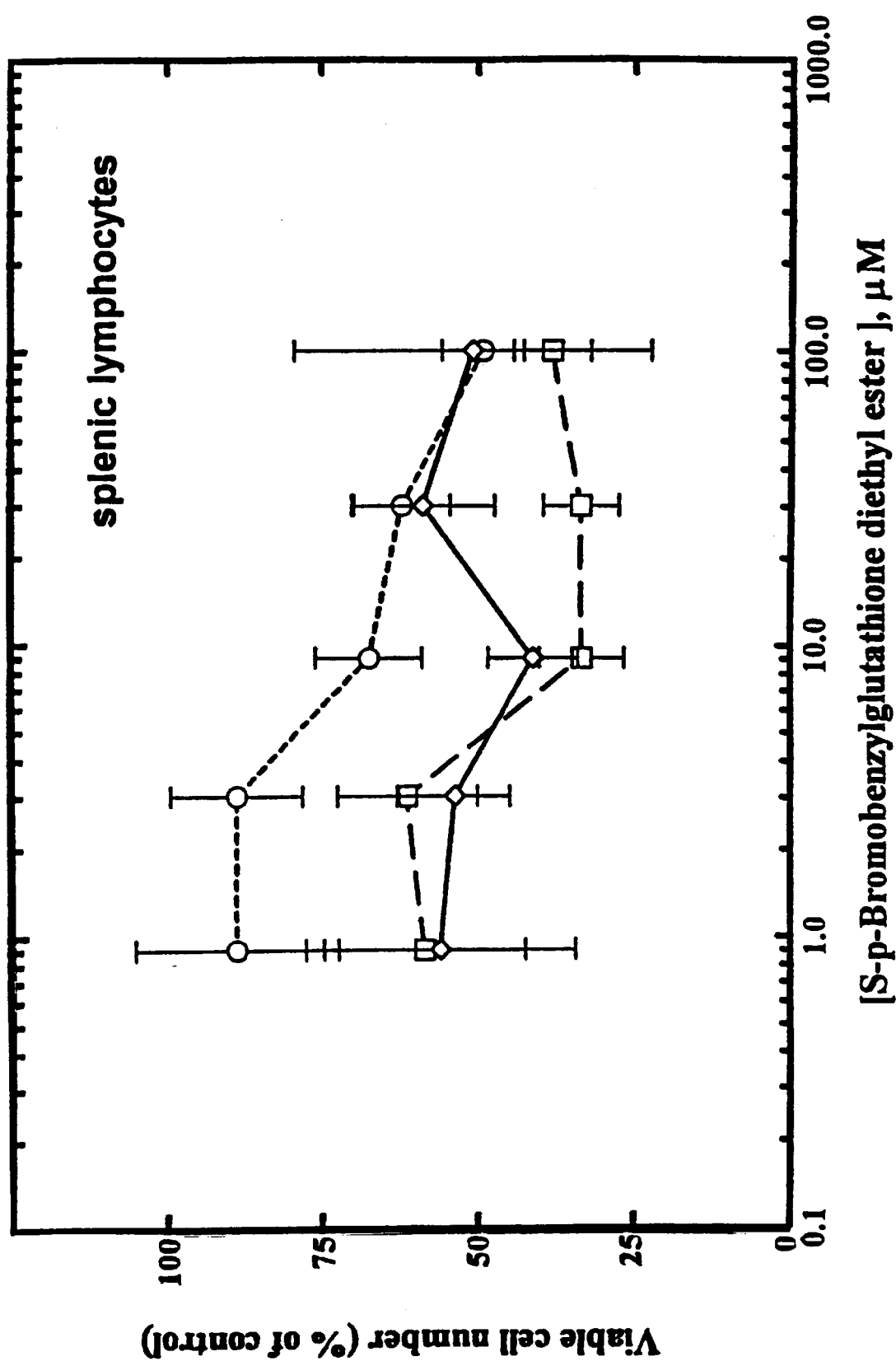

To demonstrate that dialkyl esters of GSH-based inhibitors of GlxI are antitumor agents, the diethyl esters of the mechanism-based competitive inhibitors of GlxI shown in FIG. 2 were prepared. Previously, these N-hydroxycarbamoyl esters of GSH (1–3) were shown to be hydrophobic analogs of the tightly bound enediol(ate) intermediate (GSC(OH)=C(OH)CH$_3$) that forms along the reaction pathway of GlxI (16,17). As a consequence, they are the strongest competitive inhibitors of human GlxI yet described, Table 1. The diethyl esters of the strongest inhibitors, 2(Et)$_2$ and 3(Et)$_2$, inhibited the growth of both murine leukemia L1210 and B16 melanotic melanoma cells in vitro. With both cell lines there was some correlation between the $K_i$ values of the enediol analogs and the IC$_{50}$ values of the corresponding diethyl esters. S-p-Bromobenzylglutathione diethyl ester was found to be as potent as 2(Et)$_2$ and 3(Et)$_2$ with L1210 cells, but about half as potent as 3(Et)$_2$ with B16 cells, Table 1. These IC$_{50}$ values apply under conditions where fresh drug is added to the tissue culture medium at 0, 12, 24, and 36 hours, in order to compensate partially for spontaneous deethylation of the compounds in the culture medium ($T_{1/2}$=2.5(0.5 h), as monitored by reverse-phase HPLC. The diacids 1–3 were found to be much less toxic to both cell lines, consistent with the hypothesis that these compounds do not readily diffuse into cells.

TABLE I

Growth inhibition properties of different glyoxalase I inhibitors with murine leukemia 1210 and B16 melanotic melanoma cells in culture

| Inhibitor | $K_i^a \mu M$ | L1210 $IC_{50}^b \mu M$ | $[n]^c$ | B16 $IC_{50}^b \mu M$ | $[n]^c$ |
|---|---|---|---|---|---|
| 1(Et)$_2$ | 0.16 | 78 ± 46 | 3 | <200 | 1 |
| 2(Et)$_2$ | 0.046 | 9.5 ± 3.8 | 6 | 28 ± 7 | 3 |
| 3(Et)$_2$ | 0.014 | 9.3 ± 3.4 | 3 | 5.9 ± 2.1 | 3 |
| p-BrbzylSG(Et)$_2^d$ | 0.17 | 9.8 ± 3.2 | 4 | 15 ± 5 | 3 |

$^a$Competitive inhibition constants of the unethylated species with human erythrocyte GlxI (17).
$^b$IC$_{50}$, concentration that produces 50% growth inhibition compared to no-drug controls.
$^c$Number of different experiments from which the mean and standard deviation are calculated.
$^d$S-p-bromobenzylglutathione diethyl ester. Cells were incubated for 48 h in RPMI 1640/10% fetal calf serum (37° C.) in the absence and in the presence of enzyme inhibitor. After the initial addition of inhibitor at time zero, fresh inhibitor was added every 12 h in order to compensate partially for the loss of inhibitor due to spontaneous hydrolytic deethylation in the growth medium.

In comparison to rapidly proliferating L1210 cells, non-proliferating splenic lymphocytes are significantly less sensitive to the diethyl esters. This is illustrated for 2(Et)$_2$ and S-p-bromobenzylglutathione diethyl ester by the dose-response curves of FIG. 3. For example, 2(Et)$_2$ at a concentration of 100 $\mu$M produces nearly 100% killing of L1210 cells, but decreases the viability of splenic lymphocytes by less than 50%; similar results were obtained with 3(Et)$_2$. S-p-Bromobenzylglutathione diethyl ester also shows selective toxicity towards these cell lines. Enediol analogs might exhibit selective toxicity toward tumors because these compounds are catalytically decarbamoylated in the presence of GlxII, an enzyme activity that others report is abnormally low in some types of tumor cells (16). Therefore, tumor cells might not be able to detoxify the inhibitors as rapidly as normal cells. In order to determine whether this could be a factor in the present study, the glyoxalase activities in both L1210 cells and splenic lymphocytes were determined. Indeed, while the GlxI activities in the two cell lines are nearly equal, the GlxII activity in L1210 cells is about 10-fold lower than that in splenic lymphocytes. The activities of GlxI and GlxII in L1210 cells were respectively 0.31±0.03 U/mg and 0.02±0.003 U/mg, while the activities in splenic lymphocytes were respectively 0.36±0.03 U/mg and 0.20±0.03 U/mg.

EXAMPLE 4
Cell Permeability Studies Using Diethyl Esters

Figure 4:
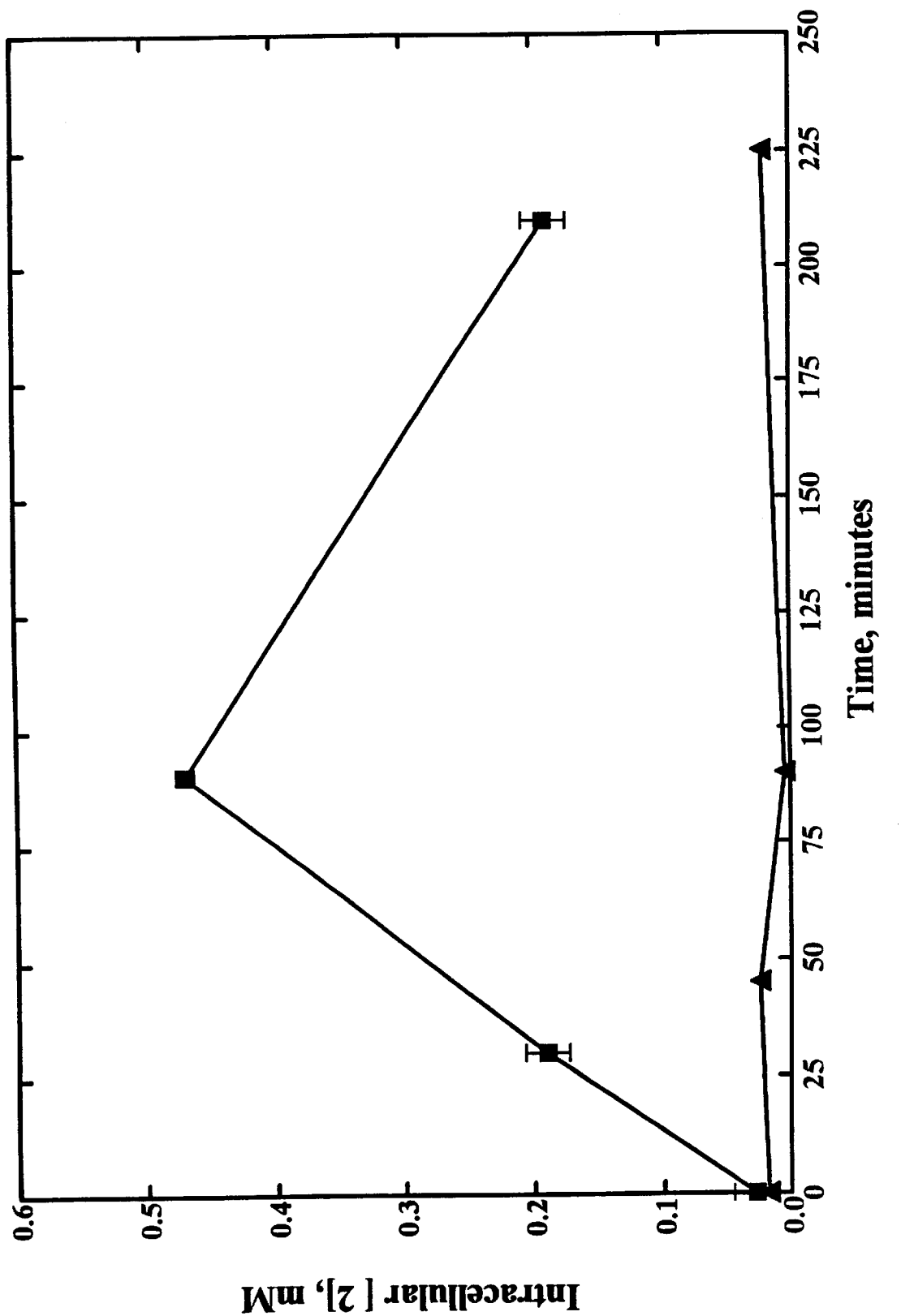
FIG. 4 shows the time-dependent change in the intracellular concentration of S-(N-p-chlorophenyl N-hydroxycarbamoyl)glutathione (2) in L1210 cells incubated in the presence of either 0.15 mM 2 (triangles) or 0.15 mM diethyl ester 2(Et)$_2$ (squares). Error bars represent standard deviations for triplicate determinations.
Figure 5:
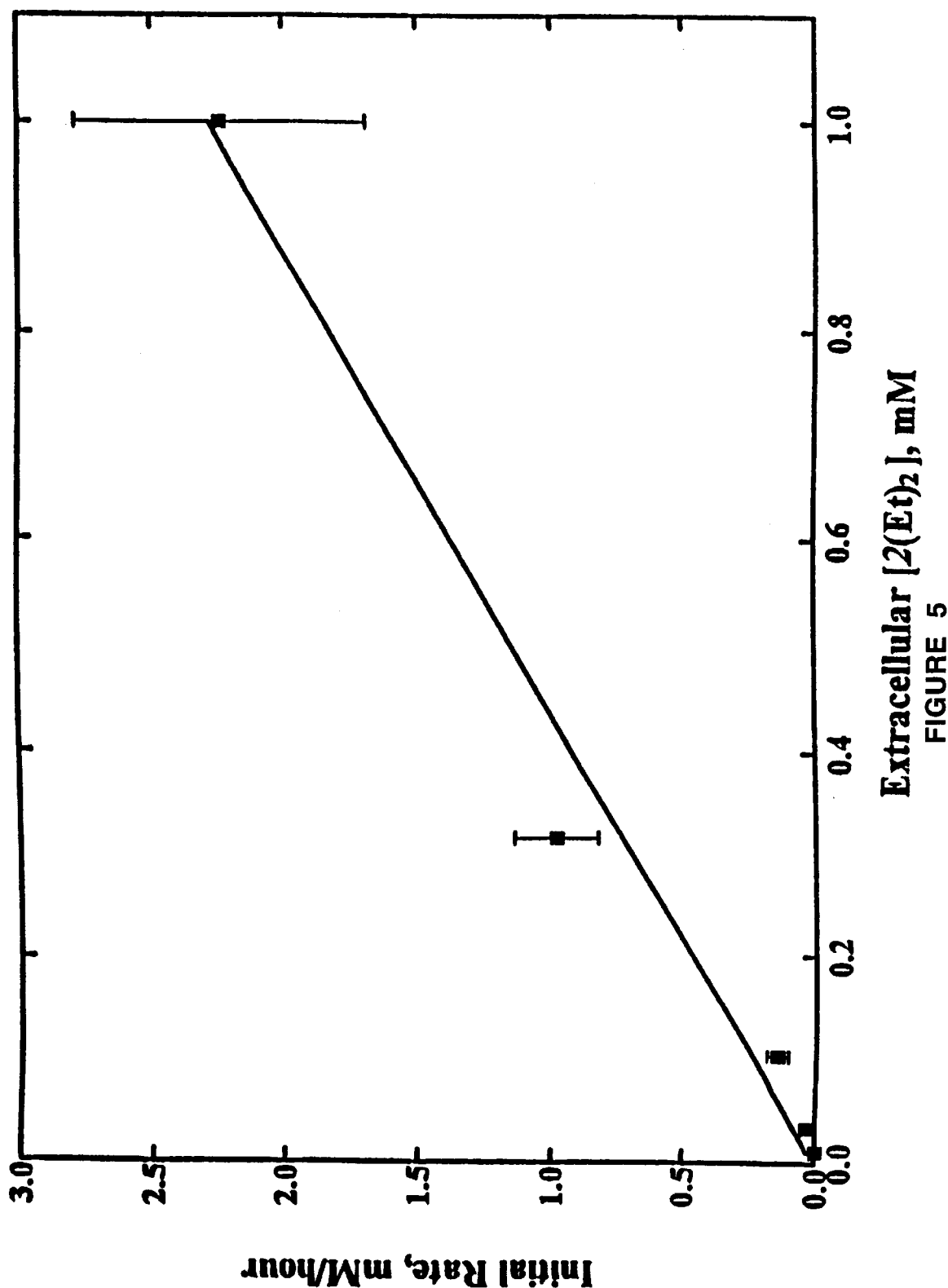
FIG. 5 shows the rates of appearance of intracellular of S-(N-p-chlorophenyl N-hydroxycarbamoyl) glutathione (2) in L1210 cells as a function of extracellular [2(Et)$_2$]. Error bars represent standard deviations for triplicate determinations.

In order to understand the mechanism of intracellular delivery of the enediol analogs, suspensions of L1210 cells were separately incubated with the diacid 2 and with the corresponding diethyl ester $2(Et)_2$. The rate of appearance of these species in the intracellular fraction was then monitored as a function of time by reverse-phase HPLC (FIG. 4). For cells incubated with 2 there was no significant time-dependent increase in intracellular [2] over the course of the experiment, indicating that L1210 cells are relatively impermeable to the diacid. In contrast, cells incubated with $2(Et)_2$ showed a rapid increase in intracellular [2] during the first 90 min. After 90 minutes, the concentration of 2 decreased, possibly due to a combination of factors including (a) 10–20% cell death over the course of the experiment, (b) hydrolytic deethylation of extracellular $2(Et)_2$, and (c) GlxII-catalyzed decarbamoylation of intracellular 2. Only trace amounts of the monoethyl esters and diethyl ester of 2 were found in the intracellular fractions. The initial rate of appearance of 2 inside the cells was found to be a linear function of extracellular $[2(Et)_2]$ in the range 0.01 to 1.0 mM (FIG. 5).

EXAMPLE 5
Stability of $2(Et)_2$ in Human Serum and Mouse Serum

Figure 6:
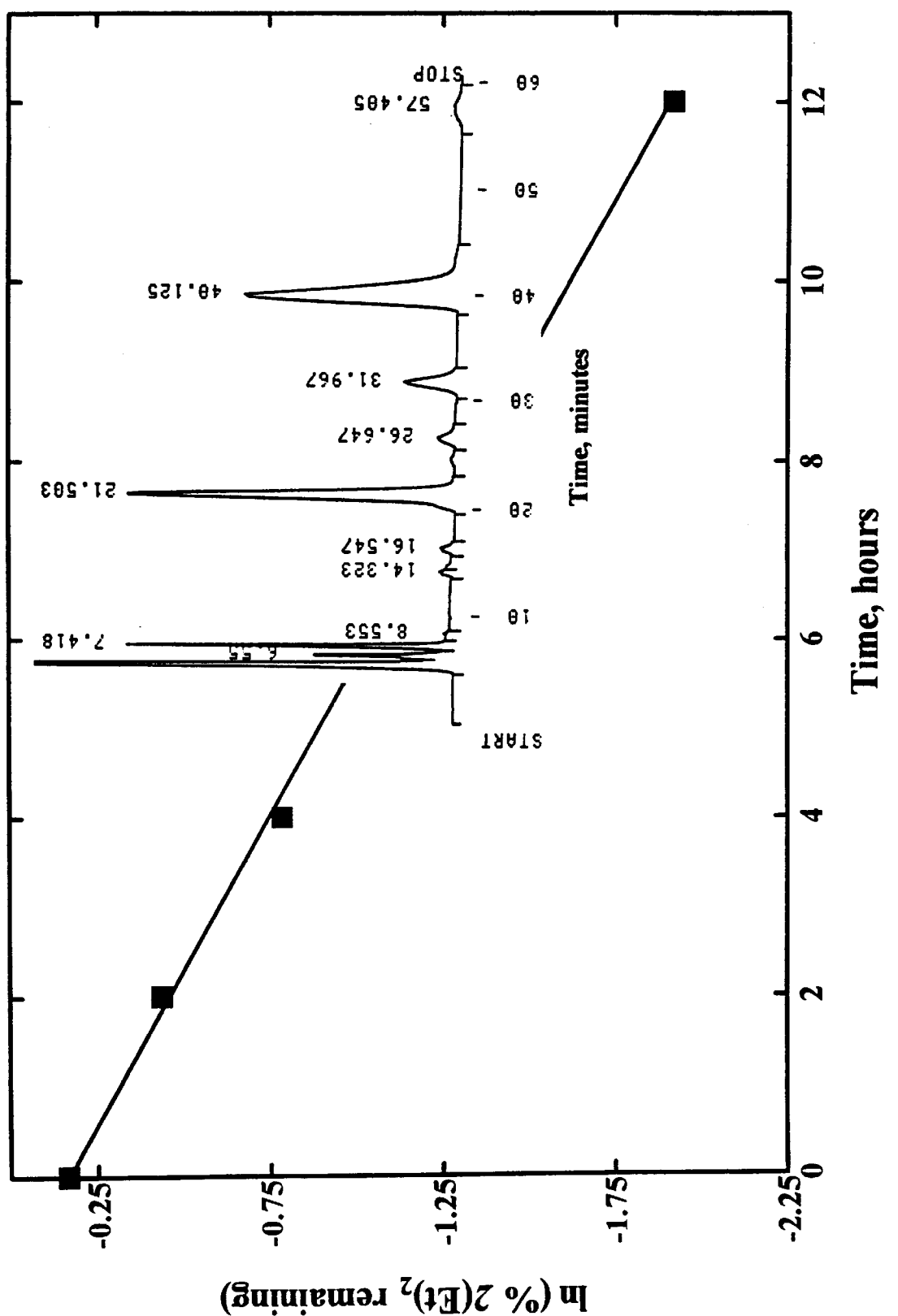
FIG. 6 shows the first order rate plot for the deethylation of S-(N-p-chlorophenyl N-hydroxycarbamoyl) glutathione diethyl ester (2(Et)$_2$) in human serum: k=0.147±0.015 h$^{-1}$, 37° C. Inset: Elution profile from a reverse-phase $C_{18}$ column (2.2×50 cm), λ=259 nm, of a deproteinized sample of human serum previously incubated with 0.1 mM 2(Et)$_2$ for 4 hours, 37° C. Running solvent: MeOH:H$_2$O (1:1) containing 0.25% acetic acid. Retention times: 2(Et)$_2$, 40.1 min; the peaks at 32.0 min and 26.6 min are assigned to the glycyl and glutamyl monoethyl esters of 2.

To identify a murine model suitable for in vivo testing of the GlxI inhibitors, the stability of $2(Et)_2$ was evaluated in human serum and in serum samples obtained from different strains of tumor-bearing mice. In human serum, $2(Et)_2$ undergoes slow first-order hydrolysis to a mixture of diacid and monoethyl esters, as monitored by reverse-phase HPLC (FIG. 6). For serum samples obtained from four different individuals, $T_{1/2}=9.1\pm5.3$ hours (n=4). In contrast, $2(Et)_2$ undergoes extremely rapid deethylation ($T_{1/2}<30$ s) in serum samples obtained from the following strains of laboratory mice, routinely used to evaluate chemotherapeutic agents against murine tumors and human tumor xenografts: DBA/2, C57BL/6, NCr nu/nu and $CD_2F_1$. In contrast, the stability of $2(Et)_2$ in serum samples obtained from plasma esterase-deficient DBA/2(C57BL/6 mice (Jackson Laboratories) was found to be similar to that in human serum: $T_{1/2}=3.9\pm0.6$ h (n=5).

Figure 9:
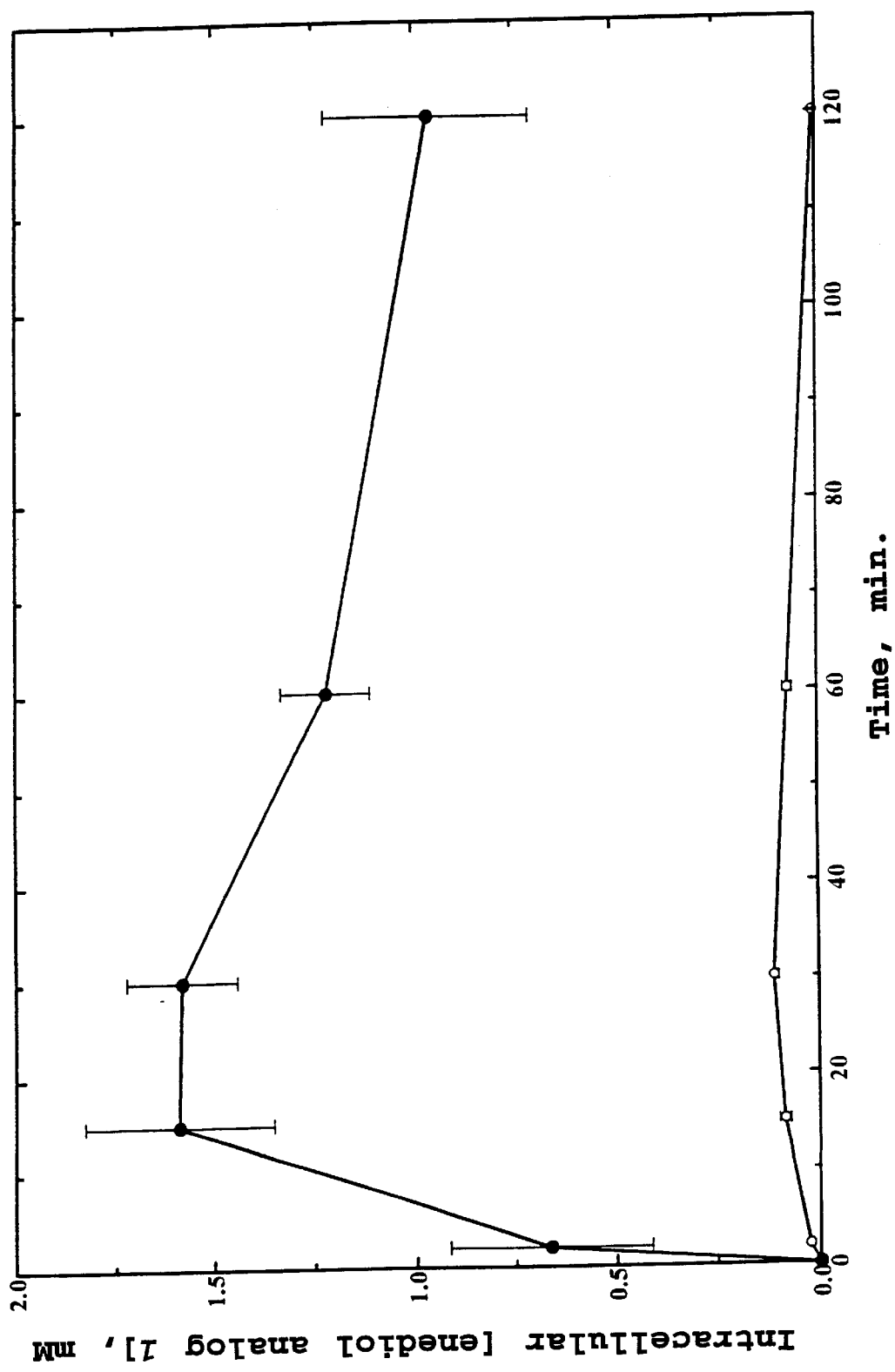
FIG. 9 shows the time-dependent change in the intracellular concentration of S-(N-p-chlorophenyl-N-hydroxy carbamoyl)glutathione (1) in L1210 cells incubated with 0.19 mM S-(N-p-chlorophenyl-N-hydroxycarbamoyl) ethylsulfoxide (3a) (closed circles), and in the presence of 0.01 mM 3a (open circles). Error bars represent standard deviations for quadruplicate determinations.

The diethyl esters of the enediol analogs shown in FIG. 9 are both cytostatic and cytotoxic to murine leukemia L1210 and B16 melanotic melanoma cells in culture (Table II). In contrast, the diethyl esters exhibits only limited toxicity toward normal nonproliferating splenic lymphocytes.

The diethyl esters constitute an effective prodrug vehicle for delivering the enediol analogs into cells (FIG. 11). During the transport studies with L1210 cells, only trace amounts of the monoethyl esters and diethyl ester of 2 were found in the intracellular fractions. This indicates that the rate of appearance of 2 inside the cells is limited primarily by the rate of transfer of $2(Et)_2$ across the cell membrane; deethylation must be a comparatively rapid process. In addition, deethylation must also be rapid in comparison to the rate of GlxII-catalyzed hydrolysis of the carbamoyl function of 2, in order to account for the high concentration of 2 inside these cells. The diethyl ester is probably transported into the cells by passive diffusion, as there is no evidence for saturation kinetics and, therefore, no reason to believe that transport is a protein-mediated process (FIG. 12).

Consistent with a passive-diffusion model, the diethyl ester $2(Et)_2$ is a lipophilic molecule, having an n-octanol/water partition coefficient ($p=9.9\pm1.1$) that is at least 990-fold larger than that of the unesterified species 2 ($p<0.01$). This prodrug strategy seems to be general for GSH and its S-conjugates. Meister and coworkers were the first to use this approach to deliver GSH, as the [glycyl] monoethyl ester, into different tissues of living mice (21,22). Subsequent studies by Lo and Thornalley indicate that the GlxI inhibitor S-p-bromobenzylglutathione can be delivered into human leukemia (HL60) cells in culture (13). The dicyclopentyl ester of S-p-bromobenzylglutathione was subsequently reported to be twice as potent as the diethyl ester with this cell line (14). This might reflect differences in the rates of intracellular delivery and/or susceptibility to deethylation by intracellular esterases.

This prodrug strategy can be used to concentrate the enediol analogs inside tumor cells. The results of the cell permeability studies show that the maximum concentration of 2 inside L1210 cells exceeds by about three-fold the extracellular concentration of $2(Et)_2$ (FIG. 11). Therefore, the rate constant for influx of the diethyl ester significantly exceeds that for efflux (and catabolism) of the diacid. This could be explained by the large difference in lipophilicities of the diethyl ester (p=9.9) and the diacid (p(0.01). However, efflux of the diacid might not involve passive diffusion across the cell membrane. Evidence has recently been found for the presence of an ATP-dependent GSH conjugate "export pump" in different tumor cell lines (23), including L1210 cells (24). This pump could potentially function to remove GSH conjugates from tumor cells. Nevertheless, under the conditions of the cell permeability studies, this pump is unable to overcome the rapid influx of enediol analog as the diethyl ester.

The cytotoxicities of the diethyl esters $1(Et)_2$-$3(Et)_2$ to L1210 and B16 melanotic melanoma cells can be reasonably attributed to the accumulation of methylglyoxal resulting from inhibition of GlxI by the enediol analogs 1–3. This is consistent with the observations that (a) the enediol analogs are powerful competitive inhibitors of purified human GlxI (Table II), (b) incubation of L1210 cells in the presence of $2(Et)_2$ gives rise to high intracellular concentrations of the corresponding diacid 2, and (c) exogenous methylglyoxal is known to inhibit the growth of tumor cells in tissue culture (5–8). In addition, Thornalley and coworkers report that incubation of HL60 cells in the presence of the dicyclopentyl ester of S-p-bromobenzylglutathione increased the measured concentration of intracellular methylglyoxal (15). However, the following caveat must be added. There is no simple relationship between the $IC_{50}$ values of the diethyl esters with the two tumor cell lines and the $K_i$ values of the corresponding enediol analogs with human GlxI. For example, enediol analog 1 and S-p-bromobenzylglutathione have nearly identical $K_i$ values, but the $IC_{50}$ value for $1(Et)_2$ is about 8-fold larger than that for S-p-bromobenzylglutathione diethyl ester. This does not exclude the possibility that inhibition of GlxI is the basis of cytotoxicity, but suggests that the $IC_{50}$ values reflect other factors like differences in cell permeabilities and rates of intracellular deethylation.

Cytotoxicity might also arises from inhibition of GlxII. Enediol analogs function as apparent competitive inhibitors of bovine liver GlxII, as these compounds are only slowly hydrolyzed by this enzyme (17). Thus, inhibition of GlxII would give rise to elevated steady-state levels of S-D-lactoylglutathione inside cells. Indeed, this metabolite inhibits the growth of HL60 cells in culture (25). Principato recently demonstrated that S-fluorenylmethoxycarbonyl glutathionediisopropyl ester inhibits the growth of rat adrenal pheochromocytoma PC-12 cells in culture with an $IC_{50}$ of 275 $\mu$M (26). This might be due to the accumulation of S-D-lactoylglutathione, as the $K_i$ value of S-fluorenylmethoxycarbonyl-glutathione obtained with a PC-12 cell extract of GlxII is about 3-fold smaller than that obtained with a PC-12 cell extract of GlxI. However, this explanation seems less likely, because the $K_i$ values of the enediol analogs with GlxII are approximately 100-fold larger than those with GlxI (17). This would preclude the accumulation of S-D-lactoylglutathione, assuming that both enzymes are equally accessible to the inhibitor inside the cells.

Diethyl esters of the enediol analogs might exhibit selective toxicity toward tumor cells versus nonproliferating normal cells, because some types of tumor cells contain abnormally low levels of GlxII activity and, therefore, are less able to hydrolyze the enediol anologs (16,17). Both $2(Et)_2$ and $3(Et)_2$ are significantly more toxic to L1210 cells than to splenic lymphocytes (FIG. 10), and GlxII activity is 10-fold lower in L1210 cells than in splenic lymphocytes. The latter observation confirms reports of abnormally low levels of GlxII activity in L1210 cells (27, 28). On the other hand, S-p-bromobenzylglutathione diethyl ester also exhibits significant selective toxicity to L1210 cells (FIG. 10). Similarly, Lo and Thornalley reported that the $IC_{50}$ value of S-p-bromobenzylglutathione diethyl ester with HL60 cells is about 5-fold lower than that with nonproliferating human neutrophils (13). This compound cannot serve as a substrate for GlxII and, presumably, provides a control for toxicity resulting primarily from inhibition of GlxI, independent of any differences in GlxII levels. Therefore, the selective toxicities observed with $2(Et)_2$ and $3(Et)_2$ might be the result of either one or both of two effects—the different abilities of L1210 cells and splenic lymphocytes to hydrolytically destroy the intracellular inhibitors and/or the different susceptibilities of each cell line to the cytotoxic effects of methylglyoxal. The dose-response curves for splenic lymphocytes with $2(Et)_2$ versus with S-p-bromobenzylglutathione diethyl ester are of insufficient precision to allow a clear decision as to the relative significance of each contribution.

Finally, the discovery of a plasma esterase-deficient strain of tumor-bearing mouse allows in vivo testing of the diethyl esters of the enediol analogs. Soares first identified a new allele of the esterase locus (Es-1), designated Es-1$^e$ (29). This mutation originally arose in an inbred strain of tumor-bearing mouse, DBA/2J. Zymogram patterns show that the ES-1E esterase migrates to a position between those of ES-1A and ES-1B and has much less enzyme activity. The mutation is heritable and there is no apparent detrimental effect to the mutant-bearing animals. Importantly, the stablity of $2(Et)_2$ in serum samples obtained from esterase-deficient DBA/2(C57BL/6 mice is similar to that in human serum samples. This is an important advance on the way toward ultimately evaluating the clinical properties of these mechanism-based competitive inhibitors of GlxI.

EXAMPLE 6
Synthesis of N-Hydroxy-N-p-chlorophenylcarbamate thioethyl ester (2a).

Figure 7:
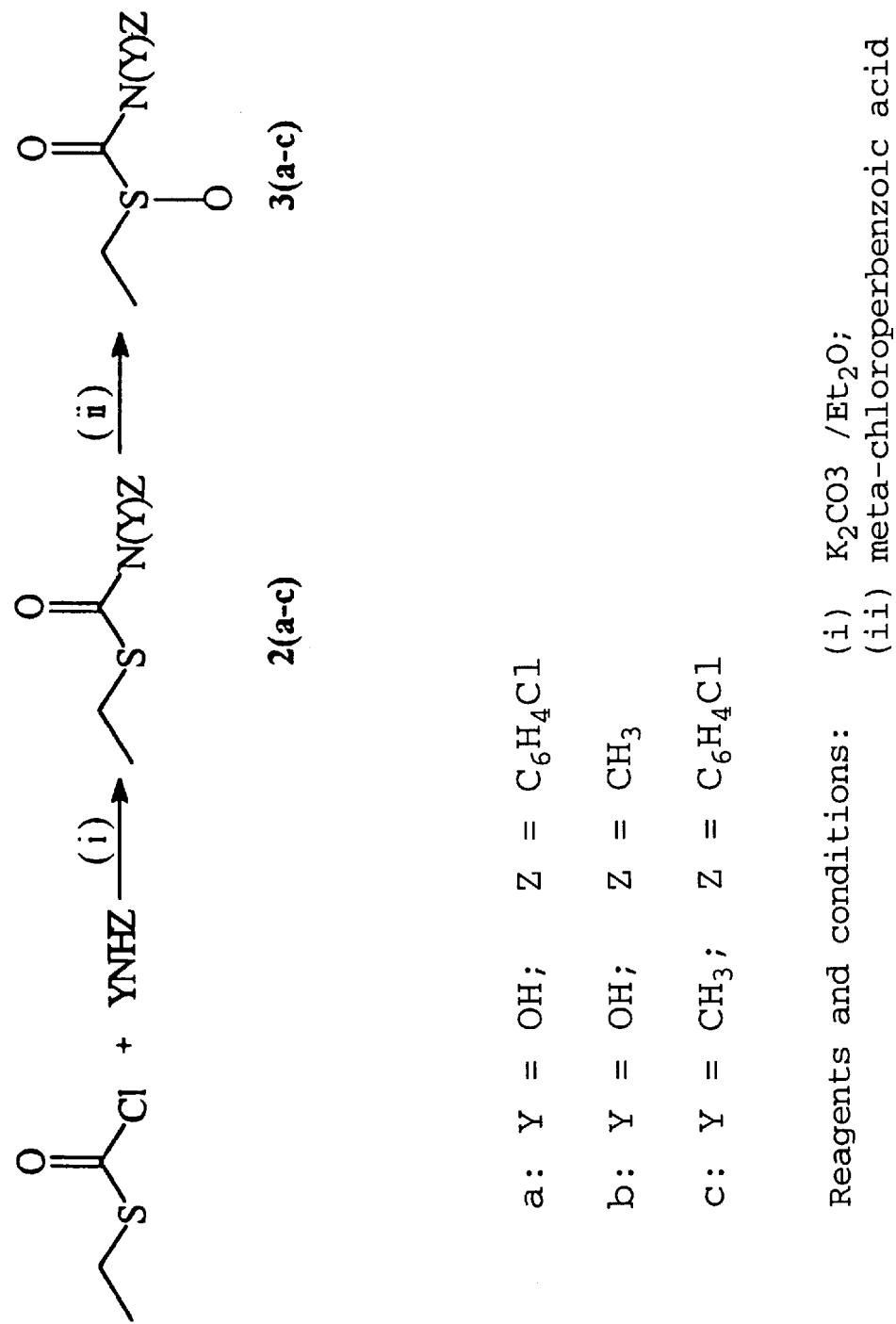
FIG. 7 shows the synthetic route to the acylating reagents shown in TABLE II.
Figure 8:
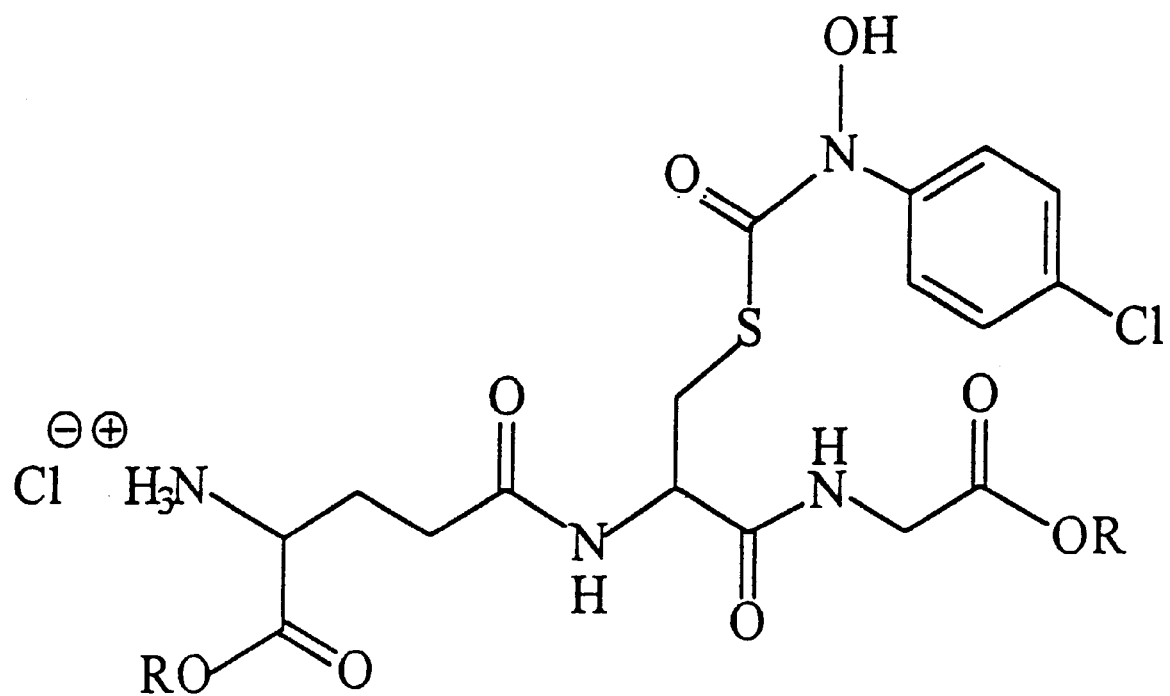
FIG. 8 shows the enediol analog S-(N-p-chlorophenyl-N-hydroxycarbamoyl)glutathione (1, R=H) and its prodrug form (1(Et)$_2$, R=$C_2H_5$). Compound 1 is a tight-binding competitive inhibitor of human glyoxalase I, $K_i$=46 nM[9].

Synthetic methods are outlined in FIG. 7. NMR spectra were taken on a GE QE-300 NMR spectrometer. Mass spectral data were obtained at the Midwest Center for Mass Spectrometry, University of Nebraska-Lincoln. Elemental analyses were obtained at Atlantic Microlabs, Inc., Norcross, Ga., and are within ±0.4% of the calculated values.

A solution of thioethyl chloroformate (0.234 g, 1.88 mmol) in diethyl ether (2 ml) is added dropwise to a ice-cold stirring mixture of N-p-chlorophenylhydroxylamine (0.27 g, 1.88 mmol), $K_2CO_3$ (0.133), diethyl ether (4 ml), and water (0.2 ml) over a period of 10 minutes. The reaction mixture was allowed to come to room temperature and followed to completion by TLC (~120 minutes). The ether layer was removed, washed with water, and dried over anhydrous $Na_2SO_4$ The solvent was removed in vacuo and the residue recrystallized from benzene/petroleum ether to give the final product as off-white needles. Yield:70%. Mp: 119° C. (decomp.). IR (KBr): 1600, 1490, 1400, 1340, 1070, 820 cm$^{-1}$. 300 M Hz $^1$H NMR (CDCl$_3$, TMS): $\delta$ 1.32 (t, J=7.5 Hz, methyl-H$_3$), $\delta$ 2.90 (q, J=7.5 Hz, methylene-H$_3$), $\delta$ 6.68 (br s, OH), $\delta$ 7.34 (d, J=8.7 Hz, p-chlorophenyl ring meta-H$_2$), (7.52 (d, J=8.7 Hz, p-chlorophenyl ring ortho-H$_2$). Anal. (ClC$_9$H$_{10}$NO$_2$S) C., H, N. Thioesters 2b and 2c were prepared by the same general method as for 2a.

EXAMPLE 7
Synthesis of S-(N-Hydroxy-N-p-chlorophenylcarbamoyl) ethyl sulfoxide (3a)

A solution of meta-chloroperbenzoic acid (84.0 mg, 0.39 mmol) in diethyl ether (2.5 ml) was added dropwise to a ice-cold stirring solution of 2a (90.2 mg, 0.39 mmol) dissolved in diethyl ether (2.5 ml) over a period of 7 minutes. After 30 minutes, the reaction mixture was allowed to come to room temperature and followed to completion by TLC (~2.5 hours). The precipitate was removed from the reaction mixture by filtration, thoroughly washed with ice-cold diethyl ether, and allowed to dry. The final product is a white powder. Yield: 90%. Mp: 143–144° C. (decomp.). IR (KBr): 1700, 1490, 1410, 1350, 1260, 1090, 1000, 800 cm$^{-1}$. 300 M Hz $^1$H NMR (d$_6$-DMSO, TMS): $\delta$ 1.20 (t, J=7.5 Hz, methyl-H$_3$), $\delta$ 7.54 (d, J=9.2 Hz, p-chlorophenyl ring meta-H$_2$), $\delta$ 7.71 (d, J=9.2 Hz, p-chlorophenyl ring ortho-H$_2$), $\delta$ 11.69 (br s, OH). HR FAB-MS consistent with ClC$_9$H$_{10}$NO$_3$S. Anal. (ClC$_9$H$_{10}$NO$_3$S) C., H, N. Sulfoxides 3b and 3c were prepared by the same general method as for 3a.

EXAMPLE 8
Cell Permeability Studies

To suspensions of L1210 cells (~1.5(10$^6$ cells/ml) in RPMI 1640 medium, containing 10% heat-inactivated fetal calf serum, gentamycin (10 $\mu$g/ml) and L-glutamate, at 37° C., were added fixed concentrations of 2a. Aliquots (1 ml) were removed from the cell suspension as a function of time, overlaid onto 0.4 ml of silicone oil (SF-1250 silicone fluids, General Electric Co., Silicone Products Division, Waterford, N.Y.) contained in an eppendorf centrifuge tube and centrifuged at 11,000×g (15 min) at 25° C. The supernatant and silicone oil were decanted from the cell pellet and residual oil removed from the inside of the centrifuge tube with a cotton swab. To the pellet was added 1 ml 70% ethanol in water and the suspension sonicated for 5 minutes. The denatured protein was sedimented by centrifugation (11, 000×g, 15 min) and the clear supernatant was removed. The supernatant was brought to dryness under a stream of argon, and the resulting residue was fractionated by reverse-phase HPLC (Waters μBondapak $C_{18}$, 0.78(30 cm), using a mobile phase composed of methanol:water (1:1) containing 0.25% acetic acid at a flow rate of 2 ml/min. The integrated intensity of the peak corresponding S-(N-p-chlorophenyl-N-hydroxycarbamoyl) glutathione was determined at λ=260 nm. Concentrations were extrapolated from standard curves that were linear in the range 0.1 to 4.0 nmoles (r=0.997).

EXAMPLE 9
Cytotoxicity Studies

Murine lymphocytic leukemia (L1210, G050141) cells were obtained from the NCI, DCT, Tumor Repository (Frederick, Md.) and were maintained in RPMI 1640 medium containing L-glutamate (Gibco BRL, Gaithersberg, Md.), supplemented with 10% heat-inactivated fetal calf serum and gentamycin (10 μg/ml), under 37° C. humidified air containing 5% $CO_2$. The L1210 cells have a doubling time of approximately 14 hours. Cells in logarithmic growth were introduced into 96-well tissue culture plates at a density of 5,000 cells/well (0.15 ml) in the absence and in the presence of at least 5 different concentrations of drug, spanning the $IC_{50}$ concentration (in triplicate). Fresh drug was added to the media every 12 hours, in order to compensate for spontaneous hydrolysis of the drug ($T_{1/2}$=4.5 h). After a 48 hour incubation period, cell densities were determined with the use of a Coulter Counter (Model ZBI, Coulter Electronics). Cell viability was determined by the trypan blue dye exclusion method.[14] The $IC_{50}$ values were obtained as computer-best-fit values to the Hill equation: $Y=100(IC_{50})^n/((IC_{50})^n+[drug]^n)$, where percent viable cell number (Y) is defined as 100(viable cells in the presence of drug)/(viable cells in no-drug controls), and n=Hill coefficient.

EXAMPLE 10
Stability of Sulfoxide 3a in Mouse Serum

To 0.5 ml portions of serum from DBA/2 mice, at 37° C., was added compound sulfoxide 3a to an initial concentration of approximately 0.8 mM. As a function of time, 0.1 ml aliquots of the incubation mixture were transferred to separate microfuge tubes. The samples were immediately deproteinized by the addition of 70% ethanol (0.9 ml). After incubation for 30 min at 37° C., the protein precipitate was sedimented by centrifugation at 13,000×g. The supernatants were then fractionated by reverse-phase HPLC μWaters (Bondapak $C_{18}$, 0.78×30 cm), using a mobile phase composed of methanol:water (1:1) containing 0.25% acetic acid at a flow rate of 2 ml/min. The integrated intensity of the peak corresponding to 3a was determined at 259 nm. The rate constant for decomposition was calculated from the first-order rate of loss of 3a as a function of time.

EXAMPLE 11
Chemistry

The acylating reagents used in the acyl-interchange reactions with glutathione were prepared as outlined in FIG. 7. Oxidation of the thioesters (2(a–c)) to the corresponding sulfoxides 3(a–c) followed the method of Casida, et al., *Science* 1974, 184, 573–574. N-(p-chlorophenyl) hydroxylamine was prepared by reduction of p-chloronitrobenzene with hydrazine hydrate in the presence of 5% Rh on carbon as described by Entwistle, et al., *Tetrahedron* 1978, 34, 213–215.

In principle, an acyl-interchange reaction might serve as the basis of an improved prodrug strategy, provided that the acylating reagent diffuses rapidly across cell membranes and then reacts rapidly with intracellular glutathione to give the enediol analog. Three N-hydroxycarbamate thioethyl esters (2(a–c)) and the corresponding sulfoxides (3(a–c)) were prepared (FIG. 7) and their rates of acyl-interchange with glutathione in a cell free system evaluated (Table II). Sulfoxidation of N,N-di-n-propylcarbamate thioalkyl esters activates these species for acyl-interchange with glutathione. Indeed, the second order rate constants for the acyl-interchange reactions with sulfoxides 3a and 3b exceed by several-fold that with the thioester 2 a. The N—OH function appears to inductively activate the sulfoxides for acyl-interchange, as the rate constant for 3a exceeds that of the corresponding N—$CH_3$ derivative 3c by 13-fold. The products of the interchange reactions were confirmed as the corresponding enediol analogs, on the basis that their UV spectra and their migratory properties on a reverse-phase $C_{18}$ column were identical with those of authentic samples of enediol analog.

TABLE II

Second order rate constants for the
acyl-interchange reactions between glutathione and the list thioesters
$CH_3CH_2XC(O)N(Y)Z + GSG \text{---}(k_2)\text{-->} GSC(O)B(Y)Z + CH_3CH_2XG$

| | Substituent | | | |
|---|---|---|---|---|
| Compound # | X | Y | Z | $k_2$, $mM^{-1}min^{-1}$ |
| 1a | S | OH | $C_6H_4Cl$ | |
| 2a | S(O) | OH | $C_6H_4Cl$ | 1.84 ± 0.07 |
| 2b | S(O) | OH | $CH_3$ | 0.59 ± 0.02 |
| 2c | S(O) | $CH_3$ | $C_6H_4Cl$ | |

Conditions: Potassium phosphate buffer (50 mM), pH 7.5, 5% ethanol, 25° C.

Cell permeability studies show that incubation of L1210 cells with sulfoxide 3a results in a rapid increase in the intracellular concentration of the corresponding enediol analog (FIG. 9). The intracellular species was isolated from the cell extracts by reverse-phase $C_{18}$ column chromatography and confirmed to be enediol analog 1 by fast-atom-bombardment tandem mass spectrometry. The first order rate constant for appearance of the enediol analog inside the cells was determined to be 1.41±0.03 $min^{-1}$, on the basis of the change in initial rate of appearance enediol analog inside the cells as a function of the extracellular concentration of sulfoxide, FIG. 10. The rate constant for influx of the neutral sulfoxide into L1210 cells exceeds by 35-fold that found for 1($Et$)$_2$. In addition, the maximum intracellular concentration of inhibitor, achieved after about 17 minutes, exceeds the extracellular concentration of the sulfoxide by greater than 10-fold, FIG. 9. Therefore, the rate constant for efflux of the enediol analog is much less than that for influx of the sulfoxide. Importantly, this provides a means of concentrating the inhibitor inside tumor cells under condition where the extracellular concentration of sulfoxide is low.

Sulfoxide 3a is also cytotoxic to L1210 cells in culture, $IC_{50}$=0.8±0.5 μM (FIG. 10). This effect can be reasonably attributed to inhibition of intracellular glyoxalase I by enediol analog, inducing elevated levels of cytotoxic methylglyoxal in the L1210 cells. The 10-fold greater potency of the sulfoxide versus the diethyl ester 1($Et$)$_2$ ($IC_{50}$=9.5 μM)[8] can be explained by the 35-fold greater rate at which the sulfoxide enters the cells in comparison to that of the diethyl ester. Cytotoxicity is unlikely to be due to depletion of intracellular glutathione because the total concentration of glutathione in L1210 cells is large in comparison to the $IC_{50}$ value. The minimum concentration of glutathione in the cells used herein was 1.6 mM, as this is the maximum concentration of enediol analog generated in these cells in the presence of 0.19 mM sulfoxide, FIG. 9. This is close to a reported value of 1.9 mM for the analytical concentration of glutathione in L1210 cells. Therefore, the concentration of glutathione will be reduced by less than 1% in the presence of a sulfoxide concentration corresponding to the $IC_{50}$, assuming that the maximum achievable concentration of enediol analog inside the cells will be about 10-fold greater than that of the extracellular sulfoxide.

Finally, sulfoxide 3a exhibits reasonable stability in serum samples obtained from DBA/2 mice, routinely used to evaluate the in vivo efficacy of drugs against L1210 cells. The first order rate constant for loss of sulfoxide from serum was determined to be 0.06±0.01 $min^{-1}$ ($T_{1/2}$=13±2 minutes), n=3. This level of stability, together with the rapid rate at which the sulfoxide diffuses into L1210 cells and the low $IC_{50}$ value, should allow the delivery of toxic levels of drug into the L1210 cells of tumor-bearing mice.

The rapid acyl-interchange reaction between glutathione and substituted N-hydroxycarbamoylethylsulfoxides is a new paradigm for indirectly delivering mechanism-based competitive inhibitors of glyoxalase I into tumor cells. In principle, this strategy could be expanded to include any S-conjugate of glutathione. The sulfoxide prodrug strategy has distinct advantages over the diethyl ester prodrug strategy, in terms of increased rates of intracellular delivery and increased potency. The improved stability of the sulfoxide, versus the diethyl ester prodrug, in mouse serum is a reflection of the fact that the sulfoxide is not an oxygen ester. These are important advances on the way towards evaluating the in vivo antitumor activities of the enediol analogs in murine models.

The present invention is directed to the use of carbasulfoxide as an anticancer agent. The name carbasulfoxide is derived from the chemical name S-(N-aryl (or alkyl)-N-hydroxycarbamoyl)thioalkyl sulfoxide. Cell growth inhibition by carbasulfoxide arises from (a) rapid diffusion of carbasulfoxide across the cell membrane, (b) reaction of intracellular carbasulfoxide with glutathione to give S-(N-aryl(or alkyl)-N-hydroxycarbamoyl) glutathiones, and (c) inhibition of the detoxifying enzyme glyoxalase I by the S-(N-aryl (or alkyl)-N-hydroxycarbamoyl) glutathiones to generate elevated concentrations of the cytotoxic metabolite methylglyoxal.

This invention provides an efficient method for generating cytotoxic inhibitors of glyoxalase I inside tumor cells via acyl-interchange with intracellular glutathione. This method is a prodrug strategy for delivering the inhibitors into cells as the membrane-permeable diethyl esters $1(Et)_2$-$3(Et)_2$. This approach functions on the basis that after the diethyl esters diffuse across the cell membrane, intracellular esterases catalytically deethylate the diethyl esters to give the inhibitory diacids, as depicted in FIG. 12.

FIG. 12 shows that the first order rate constant for appearance of 2 inside murine leukemia L1210 cells, incubated in the presence of $2(Et)_2$, was determined to be 2.2 $hr^{-1}$, on the basis of the change in initial rate of appearance 2 inside these cells as a function of the extracellular concentration of $2(Et)_2$ (FIG. 12). Sulfoxide reacts rapidly with free glutathione to generate the mechanism-based inhibitors of glyoxalase I shown below, via an acyl-interchange reaction.

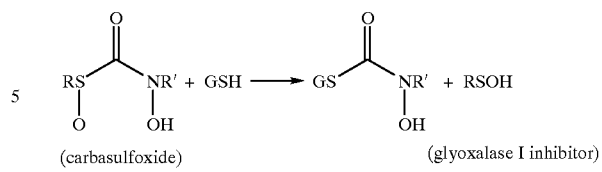
(carbasulfoxide)    (glyoxalase I inhibitor)

Where GSH=glutathione.

The prodrug sulfoxide is not susceptible to hydrolysis by esterases/peptidases and provides a rapid method for delivering the glyoxalase I inhibitors into tumor cells, via an acyl-interchange reaction with intracellular glutathione. A model of this prodrug strategy is shown in FIG. 13. Studies using murine leukemia L1210 cells in tissue culture demonstrate that the chemical invention is an exceptionally effective antitumor agent, because of the rapid rate at which it diffuses into cells, its unusual potency, and its resistance to hydrolytic degradation.

The following references were cited herein:
1. Thornalley, P., Crit. Rev. Onc. and Hematology 20, 99–128,1994.
2. Creighton, D. J., and Pourmotabbed,T. Glutathione-dependent aldehyde oxidation reactions. In Molecular Structure and Energetics: Principles of Enzyme Activity; Liebman, J. F., Greenberg, A., Eds.; VCH Publishers; Vol. 9, pp 353–386, 1988.
3. Vander Jagt, D. L. The Glyoxalase system. In Coenzymes and Cofactors: Glutathione; Dolphin, et al., O., Eds.; John Wiley and Sons; Vol. 3 (part A), pp 597–641, 1989.
4. Richard, J. P. Biochemistry 30, 4581–4585, 1991.
5. Reiffen, et al., J. Cancer Res. Clin. Oncol. 107, 206–210, 1984.
6. Ayoub, et al., Leuk. Res. 17, 397–401, 1993.
7. Baskaran, S., Biochem. Int. 212, 166–174, 1990.
8. Ray, et al., Int. J. Cancer 47, 603–609, 1991.
9. White, et al., Chem-Biol. Interact. 38, 339–347, 1982.
10. Papoulis, et al., Biochemistry 34, 648–655, 1995.
11. Ranganathan, et al., Biochem. J. 309, 127–131. 1995.
12. Vince, R., and Daluge, S. J. Med. Chem. 14, 35–37, 1971.
13. Lo, et al., Biochem. Pharmacol. 44, 2357–2363, 1992.
14. Thornalley, et al., J. Med. Chem. 39, 3409–3411, 1996.
15. Thornalley, et al., Biochem. Pharmacol. 51, 1365–1372, 1996.
16. Hamilton, et al., J. Biol. Chem. 267, 24933–24936, 1992.
17. Murthy, et al., J. Med. Chem. 37, 2161–2166, 1994.
18. Kaltenbach, et al., Exp. Cell Res. 15, 112–117, 1958.
19. Bradford, M. Anal. Biochem. 72, 248–254, 1976.
20. Fujuta, et al., J. Am. Chem. Soc. 86, 5175, 1964.
21. Anderson, et al., Arch. Biochem. Biophys. 239, 538–548, 1983.
22. Puri, et al., Proc. Nati. Acad. Sci. USA 80, 5258–5260, 1983.
23. Shen, et al., Biochemistry 35, 5719–5725, 1996.
24. Ishikawa, et al., J. Biol. Chem. 268, 20116–20125, 1993.
25. Thornalley, et al., Leukemia Research 12, 897–904, 1988.
26. Chyan, et al., Enzyme Protein 48, 164–173, 1995.
27. Jerzykowski, et al., Int. J. Biochem. 9, 853–860, 1978.
28. Ayoub, et al., Anticancer Research 13, 151–156, 1993.
29. Soares, E. R. Biochem. Genetics 17, 577–583, 1979.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound having the structure

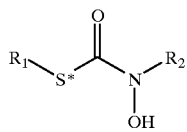

wherein S* is S=O or O=S=O;
$R_1$ is $Z_1$ or $Ar_1$; $R_2$ is independently $Z_1$ or $Ar_1$;
wherein $Z_1$ is optionally substituted with $Z_2$ or $Z_3$,
$Z_2$ is optionally substituted with $Z_3$,
$Ar_1$ is optionally substituted with $Z_4$;
and wherein
$Z_1$ is a $C_1$–$C_9$ straight or branched chain alkyl or alkenyl group;
$Z_2$ is $C_3$–$C_8$ cycloalkyl or $C_5$–$C_7$ cycloalkenyl;
$Z_3$ is $C_1$–$C_4$ alkyl, $C_1$–$C_4$ alkenyl, or hydroxyl;
$Z_4$ is halo, hydroxyl, nitro, trifluoromethyl, optionally branched $C_1$–$C_6$ alkyl, optionally branched $C_1$–$C_6$ alkenyl, $C_1$–$C_4$ alkoxy, $C_1$–$C_4$ alkenyloxy, phenoxy, benzyloxy or amino;
$Ar_1$ is selected from the group consisting of 1- or 2-naphthyl, 2- or 3-indolyl, 2- or 3-furyl, 2-thiazolyl, 2- or 3-thienyl, 2-, 3-, or 4-pyridyl, and phenyl;
or pharmaceutically acceptable salts or hydrates thereof.

2. The compound of claim 1, wherein S* is S=O, $R_1$ is $Z_1$, wherein $Z_1$ is a $C_1$–$C_9$ alkyl group and $R_2$ is $Z_1$, wherein $Z_1$ is a $C_1$–$C_9$ alkyl group.

3. The compound of claim 1, wherein S* is S=O, $R_1$ is $Z_1$, wherein $Z_1$ is a $C_1$–$C_9$ alkyl group and $R_2$ is $Ar_1$, wherein $Ar_1$ is optionally substituted with $Z_4$.

4. A pharmaceutical composition comprising the compound of claim 1 and a pharmaceutically acceptable carrier.

5. The pharmaceutical composition of claim 4, wherein said composition comprises said compound at a concentration such that from about 0.1 mg/kg to about 25 mg/kg is administered in total to a patient.

6. A method of treating an individual having a neoplastic condition comprising the step of administering to said individual a pharmacologically effective dose of the composition of claim 4.

7. The method of claim 6, wherein said composition is administered in a dose of from about 0.1 mg/kg to about 25 mg/kg.

8. The method of claim 6, wherein said neoplastic condition is selected from the group consisting of renal cancer, ovarian cancer, lung cancer, glioma and leukemia.

9. A method of inhibiting the growth of a tumor cell comprising the step of contacting said cell with a pharmacologically effective dose of the composition of claim 4.

10. A pharmaceutical composition comprising the compound of claim 2 and a pharmaceutically acceptable carrier.

11. The pharmaceutical composition of claim 10, wherein said composition comprises said compound at a concentration such that from about 0.1 mg/kg to about 25 mg/kg is administered in total to a patient.

12. A method of treating an individual having a neoplastic condition comprising the step of administering to said individual a pharmacologically effective dose of the composition of claim 10.

13. The method of claim 12, wherein said composition is administered in a dose of from about 0.1 mg/kg to about 25 mg/kg.

14. A method of inhibiting the growth of a tumor cell comprising the step of contacting said cell with a pharmacologically effective dose of the composition of claim 10.

15. A pharmaceutical composition comprising the compound of claim 3 and a pharmaceutically acceptable carrier.

16. The pharmaceutical composition of claim 15, wherein said composition comprises said compound at a concentration such that from about 0.1 mg/kg to about 25 mg/kg is administered in total to a patient.

17. A method of treating an individual having a neoplastic condition comprising the step of administering to said individual a pharmacologically effective dose of the composition of claim 16.

18. The method of claim 17, wherein said composition is administered in a dose of from about 0.1 mg/kg to about 25 mg/kg.

19. A method of inhibiting the growth of a tumor cell comprising the step of contacting said cell with a pharmacologically effective dose of the composition of claim 16.

20. The method of claim 19, wherein said tumor cell is selected from the group consisting of renal cancer cell, ovarian cancer cell, lung cancer cell, glioma cell and leukemia cell.

* * * * *